US012343564B2

(12) United States Patent
Yang et al.

(10) Patent No.: US 12,343,564 B2
(45) Date of Patent: Jul. 1, 2025

(54) IRRADIATION TERMINAL BASED ON COMBINATION OF ROTATING BEAM LINES AND APPLICATION OF THE SAME

(71) Applicant: INSTITUTE OF MODERN PHYSICS, CHINESE ACADEMY OF SCIENCES, Lanzhou (CN)

(72) Inventors: Jiancheng Yang, Lanzhou (CN); Yajun Zheng, Lanzhou (CN); Jiawen Xia, Lanzhou (CN); Wenlong Zhan, Lanzhou (CN); Zhengguo Hu, Lanzhou (CN); Hushan Xu, Lanzhou (CN); Shuang Ruan, Lanzhou (CN); Guodong Shen, Lanzhou (CN); Yaqing Yang, Lanzhou (CN); Lina Sheng, Lanzhou (CN); Qinggao Yao, Lanzhou (CN); Jinquan Zhang, Lanzhou (CN); Jie Liu, Lanzhou (CN); Ruliang Wang, Lanzhou (CN); Wei Wu, Lanzhou (CN); Wenjun Chen, Lanzhou (CN); Guimei Ma, Lanzhou (CN); Anhui Feng, Lanzhou (CN)

(73) Assignee: INSTITUTE OF MODERN PHYSICS, CHINESE ACADEMY OF SCIENCES, Lanzhou (CN)

( * ) Notice: Subject to any disclaimer, the term of this patent is extended or adjusted under 35 U.S.C. 154(b) by 0 days.

(21) Appl. No.: 18/891,471

(22) Filed: Sep. 20, 2024

(65) Prior Publication Data
US 2025/0050136 A1    Feb. 13, 2025

Related U.S. Application Data

(63) Continuation of application No. PCT/CN2023/093423, filed on May 11, 2023.

(30) Foreign Application Priority Data

Oct. 13, 2022    (CN) .......................... 202211251705.1

(51) Int. Cl.
*A61N 5/10*    (2006.01)

(52) U.S. Cl.
CPC .......... *A61N 5/1067* (2013.01); *A61N 5/1082* (2013.01)

(58) Field of Classification Search
None
See application file for complete search history.

(56) References Cited

U.S. PATENT DOCUMENTS

| 4,870,287 A * | 9/1989 | Cole ........................ G21K 5/10 |
| | | 250/398 |
| 2006/0106301 A1 | 5/2006 | Kats |
| | | (Continued) |

FOREIGN PATENT DOCUMENTS

| CN | 1889995 A | 1/2007 |
| CN | 106139420 A | 11/2016 |
| | (Continued) | |

OTHER PUBLICATIONS

Written Opinion of the International Searching Authority issued in PCT/CN2023/093423; mailed Jul. 30, 2023; 11 pgs.

(Continued)

*Primary Examiner* — Marcus H Taningco
(74) *Attorney, Agent, or Firm* — HAUPTMAN HAM, LLP

(57) ABSTRACT

Disclosed are an irradiation terminal based on a combination of rotating beam lines and an application thereof, the irradiation terminal comprises a combination of rotating beam lines, a rotating gantry, and an operation room. The combination of rotating beam lines includes a rotator beam line, a horizontal beam line, and an inclined beam line at a certain angle to the ground, and can achieve irradiation at different angles; the combination of rotating beam lines is arranged on the rotating gantry, and beam allocation for a plurality of operation rooms at different azimuth angles can be implemented through rotating a single combination of beam lines by 0-360 degrees by the rotating gantry; a plurality of rotating beam lines can be combined to achieve multi-angle beam irradiation in a single operation room. The present disclosure solves the problems in the application and promotion of irradiation devices, has outstanding advantages (Continued)

such as a large number of operation rooms, multiple irradiation angles, low construction cost, and low area occupancy, and it greatly improves treatment efficiency and reduces treatment costs, and thus is a universal ion irradiation terminal design scheme.

12 Claims, 14 Drawing Sheets

(56) References Cited

U.S. PATENT DOCUMENTS

| | | | | |
|---|---|---|---|---|
| 2007/0131876 A1* | 6/2007 | Brahme | ............... | A61B 6/4429 |
| | | | | 250/492.1 |
| 2013/0066134 A1* | 3/2013 | Carol | ...................... | A61N 5/10 |
| | | | | 378/65 |
| 2014/0275699 A1* | 9/2014 | Benna | ................... | A61N 5/103 |
| | | | | 250/492.1 |
| 2017/0235855 A1* | 8/2017 | Iwata | ..................... | G06F 30/00 |
| | | | | 703/1 |
| 2021/0299479 A1* | 9/2021 | Hooftman | ............ | A61N 5/1079 |
| 2024/0066325 A1* | 2/2024 | Michaud | .............. | A61N 5/1044 |
| 2024/0416149 A1* | 12/2024 | Nakakita | .............. | A61N 5/1078 |

FOREIGN PATENT DOCUMENTS

| | | |
|---|---|---|
| CN | 106139421 A | 11/2016 |
| CN | 107596579 A | 1/2018 |
| CN | 113808775 A | 12/2021 |
| CN | 114796895 A | 7/2022 |
| CN | 114849084 A | 8/2022 |
| CN | 114867184 A | 8/2022 |
| DE | 102004025502 A1 | 12/2005 |
| JP | 2019105641 A | 6/2019 |

OTHER PUBLICATIONS

International Search Report issued in PCT/CN2023/093423; mailed Jul. 30, 2023; 9 pgs.

* cited by examiner

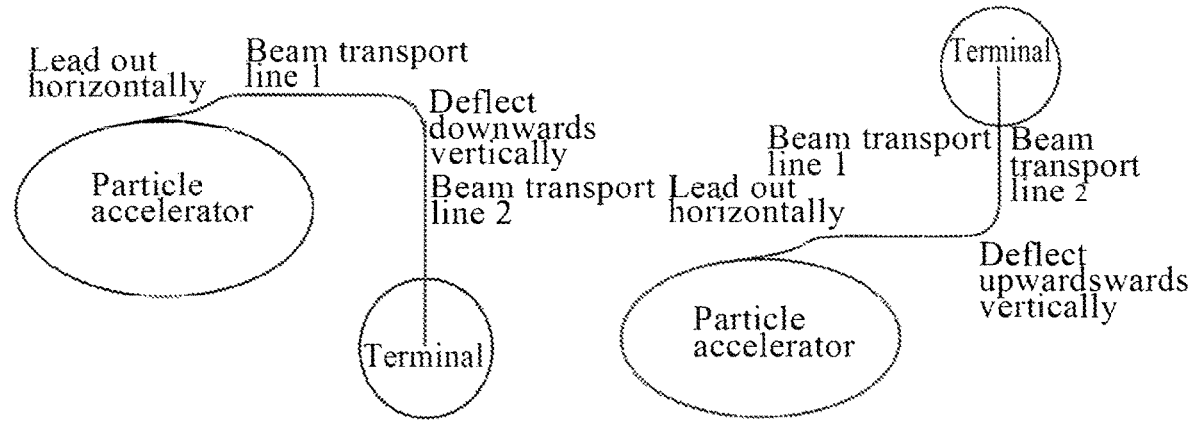
Fig. 1A
Fig. 1B
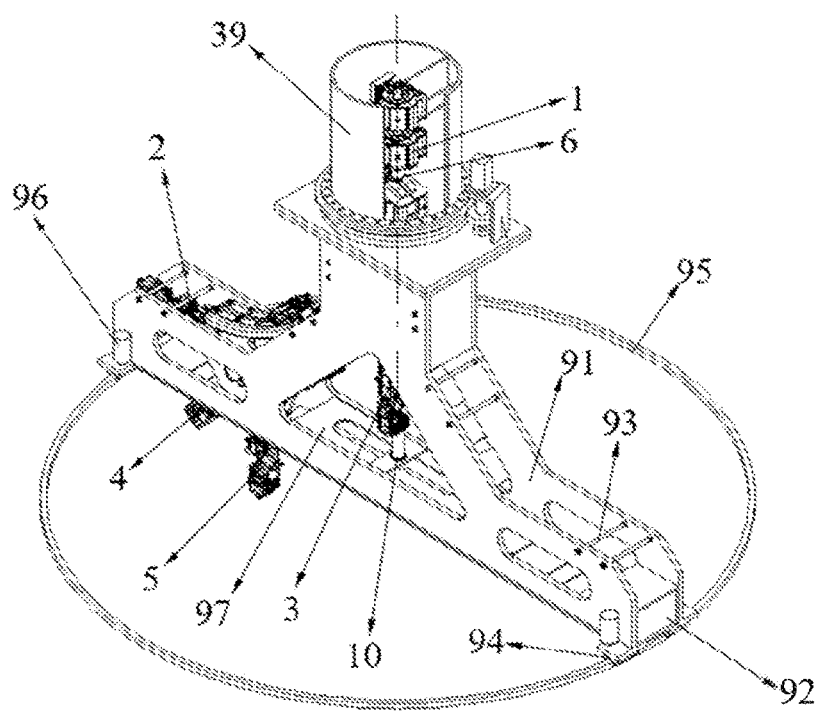
Fig. 2

IRRADIATION TERMINAL BASED ON COMBINATION OF ROTATING BEAM LINES AND APPLICATION OF THE SAME

CROSS-REFERENCE TO RELATED APPLICATIONS

This application is a Continuation of International Application No. PCT/CN2023/093423, filed May 11, 2023, which claims the priority of Chinese Patent Application CN 202211251705.1, entitled "Irradiation terminal based on a combination of rotating beam lines and an application of the same" and filed on Oct. 13, 2022, the entireties of which are incorporated herein by reference.

FIELD OF THE INVENTION

The present disclosure relates to an irradiation terminal based on a combination of rotating beam lines, and an application of the same, which belong to the field of medical treatment and irradiation technology.

BACKGROUND OF THE INVENTION

Ion beam radiotherapy and irradiation researches are widely used in the fields such as medical treatment, industry and agriculture. Presently, radiotherapy is a very popular technical means for cancer treatment applications worldwide, and the most commonly used ions for cancer ion therapy are protons and carbon. Carbon ions have more significant advantages in linear energy density, relative biological effects, and lateral scattering, and can produce DNA double stranded breaks (DSBs) that can hardly to be repaired, thereby serving as the optimal choice for cancer treatment in general.

The most time-consuming section during radiotherapy and irradiation research is pre-irradiation positioning and post-irradiation dose attenuation waiting. Increasing treatment rooms are the key bottleneck in improvement of irradiation efficiency. In an existing radiotherapy terminal, it is a single beam line that corresponds to a single treatment room, and multi-angles operation in a single treatment room is implemented through a plurality of fixed beam lines or rotating gantry technology. In this case, improvement of treatment efficiency by increasing the treatment rooms costs enormously. On a basis of 3 to 5 treatment rooms that has been commonly used internationally so far, additional treatment rooms will result in a significant cost increasing, and it is not conducive to large-scale promotion and application.

When ion beams are applying for cancer therapy, if only one radiation direction is applied, normal cells between the skin and the tumor will be subjected to at least one-third of the tumor radiation dose, and varied degrees of damage are resulted thereby. To reduce such damage and increase the focal skin ratio for treatment, a course of the treatment needs to perform irradiation from different directions and divide a total dose into a plurality of radiation directions, so that the dose to normal tissues can be significantly reduced. There are horizontal terminals, 45-degree terminals, vertical terminals, etc. For example, the first domestic heavy ion cancer therapy facility in China-Heavy Ion Medical Machine, in which the beam is extracted horizontally from synchrotron, and then climbs up and down by means of large bending magnets to create four treatment rooms, including a vertical one, a horizontal one, a horizontal-plus-vertical one, and a 45° one. As a result, the length of the extraction beam lines can reach 140 meters, and a large number of devices are used. In addition, the beam lines are climbing about 20 meters and occupy large areas, and the cost is also high.

In order to achieve multi-angle irradiation, rotating gantry technology can also be used. However, due to the high magnetic rigidity of carbon ions, the scale of the rotating gantry is very large. For example, a heavy ion rotating gantry developed by the Heidelberg Heavy Ion Research Center in Germany weighs up to 630 tons, with a rotating part weighing up to 570 tons. Moreover, a volume thereof is very large, and the manufacturing and running cost is high. Even a superconducting carbon ion rotating gantry that is being developed internationally, it still weighs over 200 tons. Rather, as the magnetic rigidity of a proton therapy device is only one-third of the magnetic rigidity of carbon ions, the weight and the volume of a gantry can be significantly reduced. An existing proton cancer treatment device usually provides rotating gantry for irradiating a patient from multiple angles. As a result, many functions are required to be implemented to enable a beam allocation system, and beam lines in the terminal are complicated, so that a weight of the rotating gantry is large, even up to a class of a hundred tons, and the entire rotating gantry is very costly.

SUMMARY OF THE INVENTION

In view of the above technical problems, the present disclosure provides an irradiation terminal based on a combination of rotating beam lines, and an application of the same. The terminal includes a combination of rotating beam lines. Compared with a conventional scheme of a fixed beam line terminal, more operation rooms can be provided in a horizontal circumferential direction of rotation of a horizontal beam line and a 45-degree (or other angles) beam line of the combination of rotating beam lines. The operation rooms are arranged in two layers, i.e., an upper layer and a lower layer, so that the number of operation rooms is increased significantly. One combination of rotating beam lines fixed on a rotating gantry can be provided with a plurality of operation rooms, which greatly improves treatment efficiency; a plurality of combination of rotating beam lines fixed on at least two rotating gantries can enable simultaneous irradiation of treatment heads at multiple angles (vertical-plus-horizontal, or 45-degree-plus-horizontal) in one operation room. The problem of significant increase of beam lines due to provision of terminal operation rooms with different irradiation angles can be solved, and the area occupancy and the investment in beam line equipment can be reduced, thereby meeting the requirement regarding miniaturization of treatment terminal systems, and facilitating promotion and application.

To achieve the above objectives, the present disclosure adopts the following technical solutions.

An irradiation terminal based on a combination of rotating beam lines, comprising:
   a combination of rotating beam lines, which is fixed on a first rotating gantry, and includes a rotator beam line and terminal beam lines, wherein the terminal beam lines include a horizontal beam line and an inclined beam line at a certain angle to the ground, the horizontal beam line and the inclined beam line are branches of the rotator beam line;
   the first rotating gantry, including two end girders and two parallel arranged main girders, wherein the two end girders are arranged in gaps at both ends of the two main girders and connected the two main girders together;

a number of first operation rooms, which are uniformly arranged along a circumferential direction of rotation of the horizontal beam line and form a first layer of operation rooms, a wall of each of the first operation rooms being provided with an installation hole;

a number of second operation rooms, which are uniformly arranged along a circumferential direction of rotation of the inclined beam line and form a second layer of operation rooms, a wall of each of the second operation rooms being provided with an installation hole;

a number of irradiation heads, which respectively correspond to the first operation rooms and the second operation rooms in a one-to-one manner, wherein the irradiation heads pass through installation holes to receive ion beams transmitted by the combination of rotating beam lines and then perform irradiation on a patient or sample; and a driving mechanism which is connected to the first rotating gantry in a transmission manner and is configured to drive the first rotating gantry to rotate 0-360 degrees along a circular guide rail, so that the combination of rotating beam lines form as beam lines that can rotate 0-360 degrees.

In the irradiation terminal, preferably, the terminal beam lines further includes a first vertical beam line and a second vertical beam line, both of which are branches of the rotator beam line.

In the irradiation terminal, preferably, a flange of an ion beam output of each of the horizontal beam line, the inclined beam line, and the second vertical beam line is equipped with a first vacuum film window, a flange of a receiving end of each of the irradiation heads is equipped with a second vacuum film window, the first vacuum film window and the second vacuum film window are configured to enable vacuum sealing between the combination of rotating beam lines and the irradiation heads.

In the irradiation terminal, preferably, a size of a gap between the first vacuum film window and the second vacuum film window is 5-200 mm.

In the irradiation terminal, preferably, the first vertical beam line is mechanically connected to the first rotating gantry by means of a thrust bearing.

In the irradiation terminal, preferably, each of the main girders includes a vertical girder, a horizontal girder, and two inclined girders connecting the vertical and horizontal girders, the horizontal girders of the two main girders are connected together through a connecting shaft and a connecting plate, and the combination of rotating beam lines is assembled in a cavity formed by the two main girders.

In the irradiation terminal, preferably, the irradiation terminal further comprise moving parts, the moving parts include a slider and a connector which are interconnected with each other, the slider is slidably connected to the circular guide rail, and the connector is connected to the driving mechanism in a motion transmission manner.

In the irradiation terminal, preferably, the rotator beam line enables rotation by means of a rotating mechanism, the rotating mechanism includes a rotating cylinder, a large gear, a gear shaft, and a positioning shaft, wherein the gear shaft and the positioning shaft are securely connected to the rotating gantry, respectively, the large gear is connected to the positioning shaft through a spacer flange and a bearing, the large gear is meshed with the gear shaft, the large gear is securely connected to the rotating cylinder, the rotating cylinder is configured to fix the rotator beam line, and the rotating cylinder, the positioning shaft, and the rotating gantry each are provided with through holes for accommodating passage of the rotator beam line.

In the irradiation terminal, preferably, the rotator beam line has the same direction of rotation as the terminal beam lines, with a rotation angle of ½ of a rotation angle of the terminal beam lines, and the rotator beam line has an x-direction phase shift that is of even multiple of $\pi$ and a y-direction phase shift that is of an odd multiple of $\pi$, so as to achieve optical invariance during rotation of the terminal beam lines.

In the irradiation terminal, preferably, the number of rotating gantry is at least one, and when the number of rotating gantry is two, which are the first rotating gantry and the second rotating gantry, respectively, the two are arranged coaxially, the first vertical beam line forms a second horizontal beam line by means of a deflection dipole magnet, the second horizontal beam line is fixed on the second rotating gantry, and an irradiation head of the second horizontal beam line and an irradiation head of the second vertical beam line are located in the same operation room and form vertical and horizontal dual-angle irradiation.

In the irradiation terminal, preferably, the number of rotating gantry is at least one, and when the number of rotating gantry is two, which are the first rotating gantry and the second rotating gantry, respectively, the two are arranged coaxially, the first vertical beam line forms a second horizontal beam line by means of a deflection dipole magnet, the second horizontal beam line is fixed on the second rotating gantry, and an irradiation head of the inclined beam line and a third irradiation head of the second horizontal beam line are located in the same operation room and form inclined and horizontal dual-angle irradiation.

In the irradiation terminal, preferably, the irradiation heads and the combination of rotating beam lines are designed in an integrated manner or a separated manner.

A third aspect of the present disclosure further relates to an application of the irradiation terminal in radiotherapy and industrial irradiation.

By using the above technical solutions, the present disclosure has the following advantages:

1. The combination of rotating beam lines provided by the present disclosure is based on any type of accelerator, in which a beam is led out in any manner and then deflected vertically, and beam allocation with different irradiation angles is enabled by combining the horizontal beam lines, the first vertical beam lines, the second vertical beam lines, and the 45-degree (or other angles) beam lines. Furthermore, the combined beam lines can be rotated to achieve beam allocation for a plurality of operation rooms at different azimuth angles. The combination of rotating beam lines has a compact structure, and a length of the beam lines can be shortened by 90% compared to the conventional fixed beam lines.

2. The traditional treatment terminal is in a pattern of one beam line corresponding to one operation room, and requires four beam lines to implement beam allocation across four operation rooms, with a total length of beam lines of nearly 200 meters. The present disclosure can achieve beam allocation for more than 8 operation rooms only through a beam line of 30 meters, which not only reduces the cost of processing equipment such as magnets, vacuum, and power supply, but also lower the scale and the cost of those supporting auxiliary facilities. At the same time, the running cost during treatment of the device is also reduced significantly.

3. The present disclosure can achieve beam allocation for a plurality of operation rooms through a single rotating beam line, the rotating beam line may be a single-angle beam line or a multi-angle combined beam line. The number of operation rooms by the single-angle rotating beam line may reach more than 8. On bases of this, a combination of multi-angle rotating beam lines can be constructed, which not only expands treatment angles but also further increases the number of operation rooms. Furthermore, on the basis of the above, the rotating beam line can also be a combined structure with multiple stages, and each stage of multi-angle rotating beam line can correspond to a plurality of operation rooms, greatly improving treatment efficiency.
4. A tumor patient often requires multi-angle irradiation during once treatment to reduce the damage to normal cells encountering a beam routing path. However, the present disclosure can achieve multi-angle irradiation treatment in one operation room through a multi-stage rotating beam line. For example, dual-angle irradiation of 45-degree and horizontal, of vertical and horizontal can be implemented through two-stage rotation. As such, the tumor patient can complete the required multi-angle irradiation in only one operation room. Moreover, this multi-stage rotation combination can achieve a plurality of multi-angle operation rooms at low cost, and further significantly improve treatment efficiency.
5. The present disclosure adopts a design of separate pattern, in which the combination of rotating beam lines and the irradiation heads are designed to be separate with each other by using vacuum film window technology, thereby further reducing the rotation radius, reducing the processing and installation costs of a rotating part, and improving the motion and positioning accuracy of a rotating beam line. A vacuum film window is used between the combination of rotating beam lines and an irradiation head to enable vacuum sealing and physical space separation. An ion beams can non-destructively pass through the first vacuum film window, the atmosphere, and the second vacuum film window, in turn, from the combination of rotating beam lines to the irradiation head. The combination of rotating beam lines and the irradiation head are designed as a separate pattern, with a further reduction of 50% in the rotation radius, so that the rotation structure thereof becomes simple, the processing and installation cost is low, and the accuracy is easy to ensure.
6. Since a beam let out of a synchrotron exhibits high asymmetry in both the horizontal direction (which involves rotation in a later phase, so is replaced by the x-direction then) and the vertical direction (which involves rotation in a later phase, so is replaced by the y-direction then), in order to ensure the irradiation accuracy, it is required that a terminal beam spot would be no change during the rotation. The present disclosure uses a rotator to achieve constant optical parameters during the rotation of the terminal beam lines, which significantly reduces the difficulty of controlling terminal targets during the rotation. The rotator adopts a compact design, with a total length of only 2.5 m which is much less than an internationally available scheme with 9-10 m, thereby greatly reducing a demand of the device on a vertical space, as well as the construction difficulty and the cost of the device. Although it is a difficulty in the optical design to have multi-angled beam lines from the same rotator beam line, the present disclosure can control the dimensions of beam spot of the entire lines to be within ±16 mm by optimizing the position and strength of magnet elements, which can significantly reduce the sizes and the cost of magnets, power supply, beam diagnosis, and vacuum elements, as well as the price of related auxiliary facilities.
7. Since the beam let out of a synchrotron exhibits high asymmetry in both the horizontal direction (which involves rotation in a later phase, so is replaced by the x-direction then) and the vertical direction (which involves rotation in a later phase, so is replaced by the y-direction then), in order to ensure the irradiation accuracy, it is required that a terminal beam spot would be no change during the rotation. The present disclosure uses a rotator to achieve constant optical parameters during the rotation of the terminal beam lines, which significantly reduces the difficulty of controlling terminal targets during the rotation. Another prominent advantage of the optical design of said rotator is to adapt to arbitrarily angled terminal beam lines while maintaining small beam spot sizes for the entire lines, and the combination of rotating beam lines such as of horizontal, vertical, and 45-degree in the present disclosure can simultaneously enable optical parameters to be constant during the rotation of the plurality of arbitrarily angled terminal beam lines. The rotator adopts a compact design, with a total length of only 2.5 m which is much less than an internationally available scheme with 9-10 m, thereby greatly reducing a demand of the device with respect to a vertical space, as well as the construction difficulty and the cost of the device.
8. The irradiation terminal of the present disclosure can be connected to any type of accelerator, and provides beam allocation in multiple angles and a plurality of operation rooms at a lower cost, which further reduces the area occupancy of the device, reduces equipment investment, and improves treatment efficiency. It is not only suitable for heavy ion devices, but also for proton devices; and it is not only suitable for radiotherapy, but also for industrial irradiation. Therefore, it is a universal solution in the fields of radiotherapy and irradiation.

BRIEF DESCRIPTION OF THE DRAWINGS

FIG. 1A is a schematic diagram in which a beam is vertically deflected downwards to a terminal from a horizontal direction of a particle accelerator, and FIG. 1B is a schematic diagram in which the beam is vertically deflected upwards to the terminal;

FIG. 2 is a schematic diagram in which a combination of rotating beam lines is fixed on a rotating gantry according to an embodiment of the present disclosure;

FIGS. 4-7 are schematic diagrams in which a combination of rotating beam lines is fixed on one rotating gantry, respectively, according to several embodiments of the present disclosure, wherein FIG. 7 is a cross section view along a direction of B-B in FIG. 5;

Figure 3:
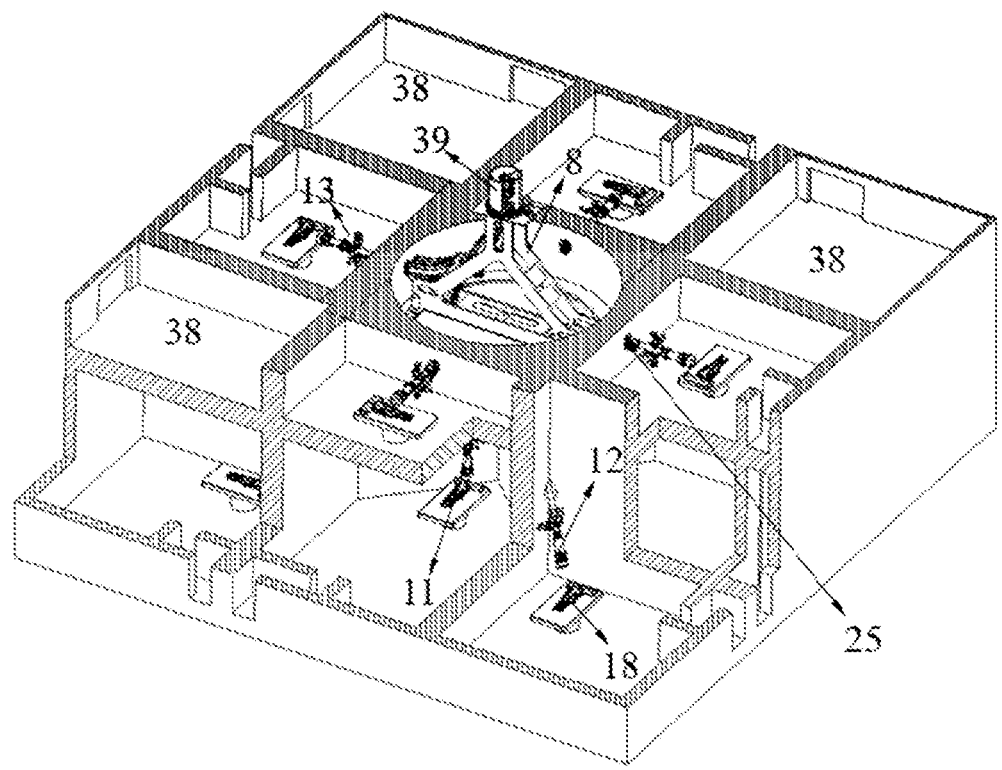
FIG. 3 is a cross section view of an irradiation system where a combination of rotating beam lines is fixed on one rotating gantry according to an embodiment of the present disclosure.

The reference numbers in the drawings are as follows:

1—Rotator beam line; 2—First horizontal beam line; 3—First vertical beam line; 4-45—degree beam line; 5—Second vertical beam line; 6—First rotary sealing device, 7—Second rotary sealing device; 8—First rotating gantry; 9—Second rotating gantry; 91—Main girder; 92—End girder; 93—Connecting shaft; 94—Moving parts; 95—Circular guide rail; 96—Driving mechanism; 97—Connecting plate; 10—Thrust bearing; 11—Vertical irradiation head; 12-45—degree irradiation head; 13—First horizontal irradiation head; 14—Third rotary sealing device; 15—Second horizontal beam line; 16—Second horizontal irradiation head; 17—Third horizontal irradiation head; 18—Therapy couch; 19—Rotation axis; 20—First vacuum film window; 21—Second vacuum film window; 22—Rotating vacuum film window axis; 23—irradiation head vacuum film window axis; 24—Circular sliding contact line; 25—Installation hole; 26-29—First to fourth horizontal operation rooms; 30-33—First to fourth 45—degrees-plus-horizontal operation rooms; 34-37—First to Fourth vertical-plus-horizontal operation rooms; 38—irradiation preparation room; 39—rotating mechanism; 391—Rotating cylinder; 392—Large gear; 393—Gear shaft; 394—Positioning shaft; 395—Motor; 396—Fixing bracket; 397—Bearing; 398—First bolt; 399—Second bolt; 3910—Spacer flange; 40—Quadrupole magnet; 41-45-degree dipole magnet.

DETAILED DESCRIPTION OF THE EMBODIMENTS

In order to make objectives, technical solutions, and advantages of the present disclosure clearer, the technical solutions of the present disclosure are described in a clear and complete manner below. Apparently, the embodiments described herein are only a part, rather than all, of the embodiments of the present disclosure. Based on the embodiments in the present disclosure, all other embodiments obtained by an ordinary person skilled in the art without creative labor should fall within the scope of protection of the present disclosure.

Unless otherwise defined, the technical or scientific terms used in the present disclosure shall have the general meaning understood by the ordinary person skilled in the art to which the present disclosure belongs. The wordings "first," "second," "third," "fourth," and the like used in the present disclosure do not indicate any order, quantity, or importance, but are merely used to distinguish different components. Wordings such as "comprise" or "include" means that a component or object that appears ahead the wording includes components, objects or their equivalents listed after the wording, without excluding other components or objects. Wordings such as "connect" or "couple" are not limited to physical or mechanical connections, but can include electrical connections, no matter of a direct or indirect manner.

In recent years, with the continuous development of accelerator technology, accelerator devices have been developed towards miniaturization and compactness, and an area occupied by a device itself is gradually decreased. To meet this regard, an effort is also made with respect to a mode that a beam is led out of the accelerator and an arrangement of beam lines.

As shown in FIGS. 1a and 1b, a particle accelerator adopts a room temperature scheme or a superconducting scheme, and can be a synchrotron, cyclotron, FFAG (Fixed-Field Alternating Gradient), linear accelerator, or other types of accelerators. In the particle accelerator, a beam may be led horizontally out of an inner portion or an outer portion, and the led beam is deflected vertically downwards along a beam transport line 1 to a beam transport line 2 and is then transmitted to a terminal. Alternatively, it is vertically deflected upwards along the beam transport line 1 to the beam transport line 2 and is then transmitted to the terminal. The beam in the particle accelerator can also be led vertically out of the outer or inner portion by means of a Lambertson (iron cutting magnet) cutting magnet.

The most time-consuming phase during radiotherapy is pre-irradiation positioning and post-irradiation dose attenuation waiting. Increasing operation rooms is a key bottleneck in improvement of treatment efficiency. In an existing radiotherapy terminal, it is a single beam line to correspond to a single operation room, and multi-angle operation of a single operation room is implemented through a plurality of fixed beam lines or rotating gantry technology. In this case, improvement of treatment efficiency by increasing the operation rooms costs enormously. On a basis of 3 to 5 operation rooms that has been commonly used internationally so far, addition of operation rooms will result in a significant increase in the cost of treatment devices, and thus is not conducive to large-scale promotion and application.

The present disclosure can achieve beam allocation for a plurality of operation rooms through a single rotating beam line. The rotating beam line may be a single-angle beam line or a multi-angle combined beam line. The number of operation rooms achieved by the single-angle rotating beam line can reach more than 8. On bases of this, a combination of multi-angle rotating beam lines can be constructed, which not only expands treatment angles but also further increases the number of operation rooms. Furthermore, on the basis of the above, said rotating beam line can also be a combined structure with multiple stages, and each stage of the multi-angle rotating beam line can correspond to a plurality of operation rooms, greatly improving treatment efficiency.

An irradiation terminal based on a combination of rotating beam lines provided by the present disclosure provides any type of accelerator that has an arrangement for leading out a beam in any manner and then deflecting it vertically (upwards or downwards) with a terminal irradiation system having multiple angles, multiple operation rooms, and single room but with multiple angles, which further reduces area occupancy of the device, lower equipment investment, and improve treatment efficiency.

The present disclosure is described in detailed below in conjunction with the accompanying drawings.

As shown in FIG. 2, a combination of rotating beam lines provided by the present disclosure includes: a rotator beam line 1; a combination of rotating beam lines that is made up of a first horizontal beam line 2, a first vertical beam line 3, and a 45-degree (or other angle) beam line 4 and a second vertical beam line 5, which are composed of conventional magnets, superconducting magnets, superconducting coils, or any combination of them; and a first rotary sealing device 6 and a second rotary sealing device 7 which connect the rotator beam line 1 and the first vertical beam line 3 together, the first and second rotary sealing devices 6, 7 being configured to maintain vacuum during rotation.

Figure 4:
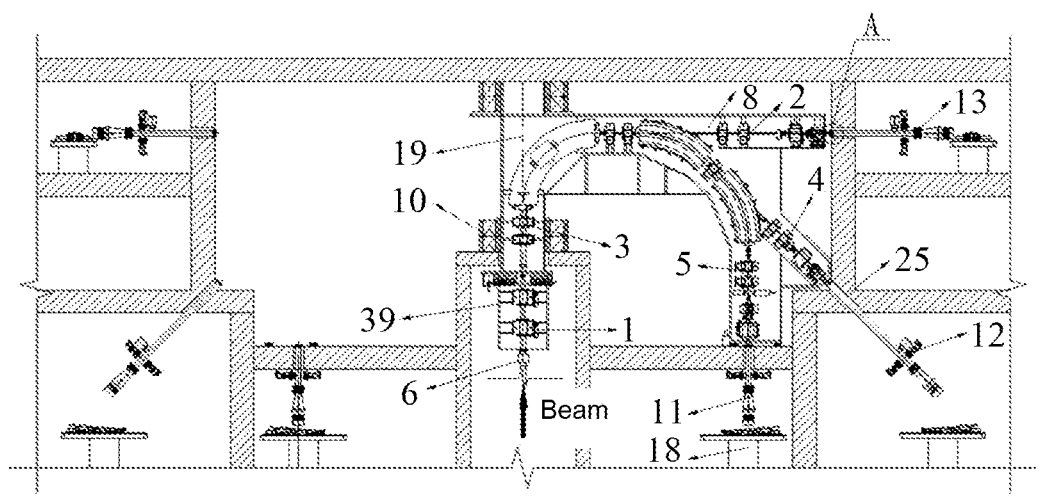
Figure 5:
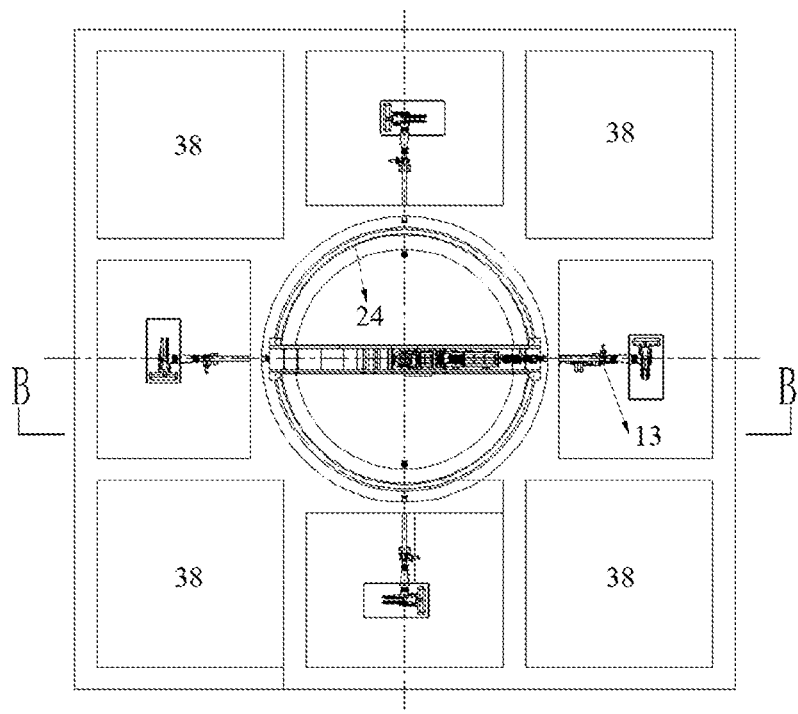
Figure 6:
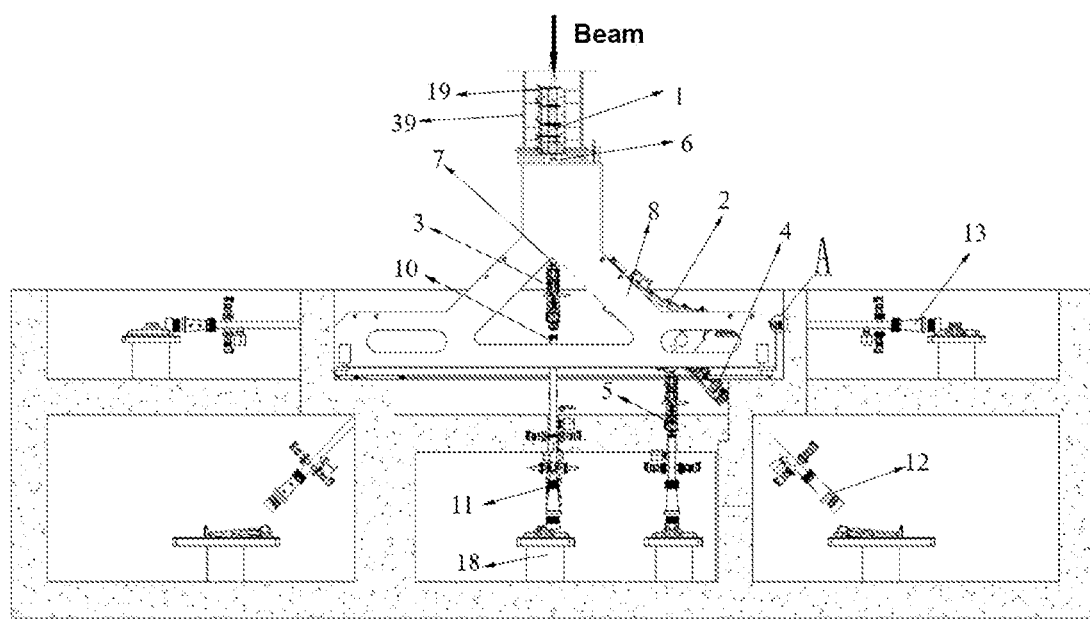
Figure 7:
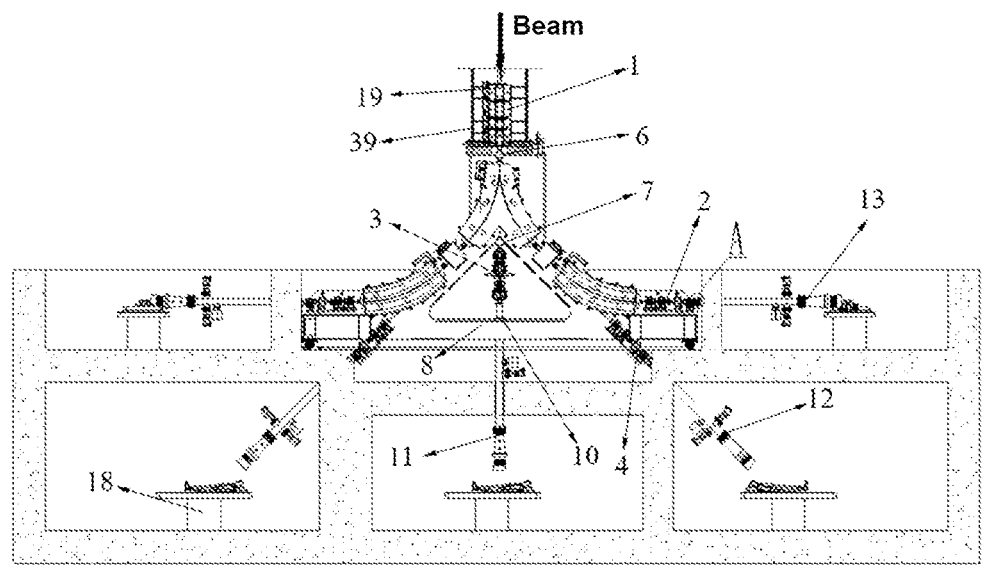
Figure 8:
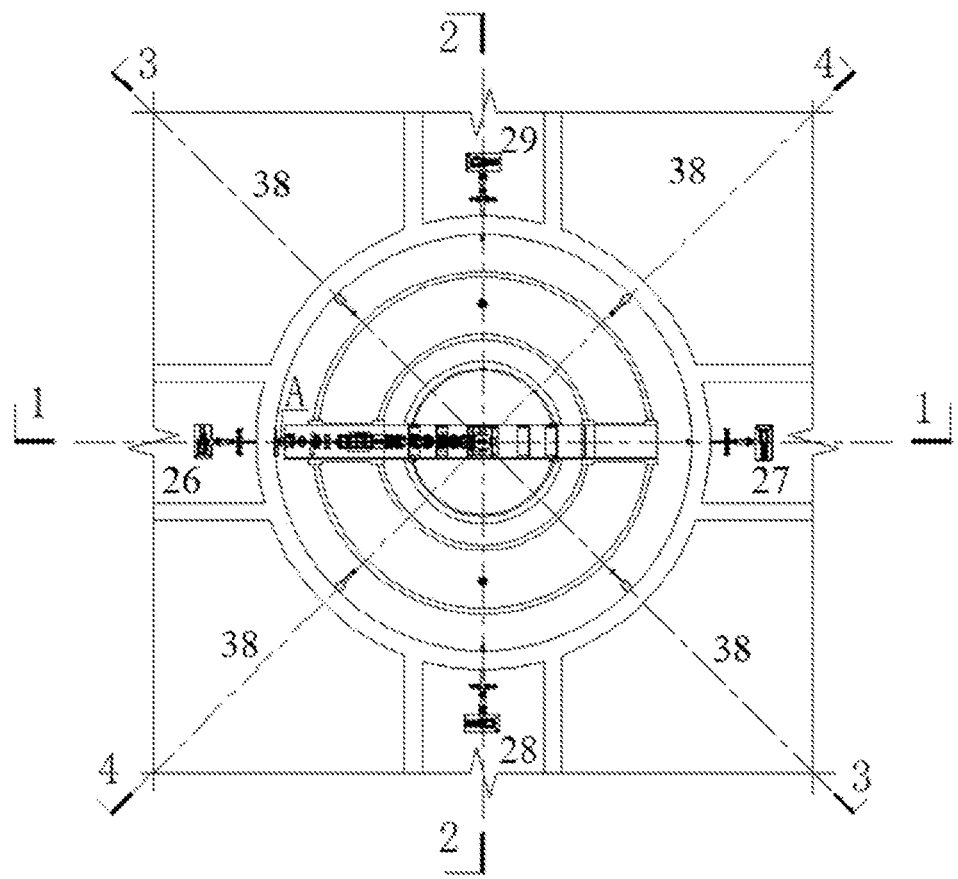
FIG. 8 is a top view in which a combination of rotating beam lines is fixed on two rotating gantries according to another embodiment of the present disclosure.

As shown in FIGS. 3-7, it is a terminal irradiation system with a single combination of rotating beam lines (beam lines being fixed on one rotating gantry). The single combination of rotating beam lines can be arbitrarily combined in accordance of deflection magnets. Although the present disclosure only lists several typical embodiments, anyone of other combination of beam lines should be included within the present disclosure. The combination of rotating beam lines is fixed on a rotating gantry and rotates under the action of a driving mechanism 96. Operation rooms are divided into two layers, i.e., an upper layer and a lower layer, and those on the upper layer are horizontal operation rooms, and the lower layer is provided with 45-degree operation rooms and vertical operation rooms. As shown in FIG. 4, this embodiment provides that a beam in the accelerator, after being led out in any manner, is deflected to a vertical direction, and then forms a combination of terminal beam lines by means of another deflection. The significant advantage of such structure is to achieve reduction of an overall height of the system. The deflection magnets and the combination of terminal beam lines are fixed on a rotating gantry, and the operation rooms with different irradiation angles are arranged in a circumferential direction of rotation. Also, it is possible to arrange, preferably, 12 operation rooms, and of course, more operation rooms can be provided in accordance of a treatment plan. As shown in FIG. 7, the combined beam line can be designed as a symmetrical structure, and the rotating gantry only needs to be rotated 180 degrees or less to achieve all irradiation angles, which helps to further shorten treatment waiting time and improve treatment efficiency.

Specifically, as shown in FIG. 3, the operation rooms of the irradiation terminal based on a combination of rotating beam lines being fixed on one rotating gantry according to the present disclosure are divided into two layers, i.e., the upper and lower layers. Those in the upper layer are horizontal operation rooms arranged in a horizontal circumferential direction of rotation of the first horizontal beam line 2. Apparently, irradiation preparation rooms 38 on the upper layer can also be horizontal operation rooms, so that it is possible to uniformly arrange 8 horizontal operation rooms. Those in the lower layer are four 45-degree (or other angle) operation rooms arranged in a horizontal circumferential direction of rotation of the 45-degree (or other angle) beam line 4. Four vertical operation rooms are arranged in a circumferential direction of rotation of the second vertical beam line 5. Preferably, the vertical operation rooms and the 45-degree operation rooms are arranged in a staggered manner. The combination of rotating beam lines can preferably be provided with 16 operation rooms.

In practice, tumor patient often requires multi-angle irradiation during once treatment to reduce the damage to normal cells encountering a beam routing path. However, the present disclosure can achieve multi-angle irradiation treatment in one operation room through multi-stage rotating beam lines. For example, dual-angle irradiation of 45-degree and horizontal and of vertical and horizontal can be implemented through two-stage rotation. As such, the tumor patient can complete the required multi-angle irradiation in only one operation room without switching back and forth between those single-angle operation rooms, thereby reducing switching time and preparation time. Moreover, this multi-stage rotation combination can achieve a plurality of multi-angle operation rooms at low cost, and further significantly improve treatment efficiency.

Figure 9:
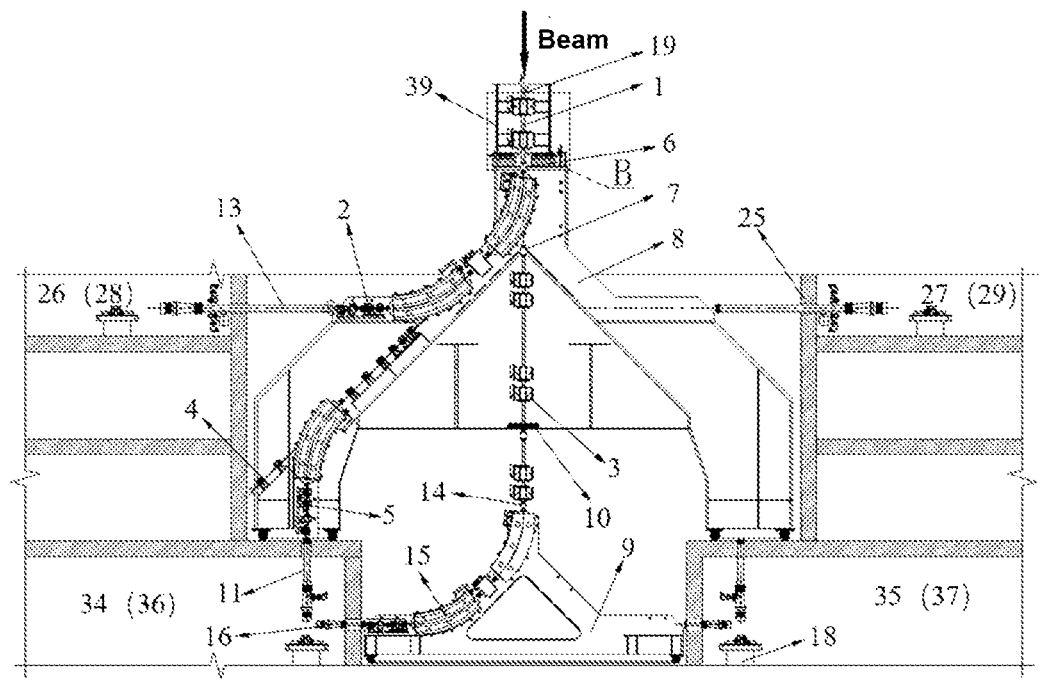
FIG. 9 is a cross section view along a direction of 1-1 or 2-2 in FIG. 8.

As shown in FIG. 9, two combinations of rotating beam lines are fixed on a first rotating gantry 8 and a second rotating gantry 9 that are vertically coaxial; the first rotating gantry 8 includes two end girders and two parallel arranged "Gantry type" main girders, and the two end girders are placed in gaps between the two main girders at both ends and mechanically connect the two main girders together; the second rotating gantry 9 includes two end girders 92 and two parallel arranged "Herringbone" main girders 91, the two end girders 92 are placed in gaps between the two main girders 91 at both ends and mechanically connect the two main girders 91 together. The main girders 91 are configured to disperse the gravity of the combination of rotating beam lines onto the end girders 92. A lower part of the end girder 92 is provided with moving parts 94 which include interconnected sliders and connectors, the connectors are connected to driving mechanisms 96 in a motion transmission manner, the sliders are connected to a circular guide rail 95 in a sliding manner, and the circular guide rail 95 guides and constrains the sliders. Connecting shafts 93 connect vertical girders as well as horizontal girders of the two main girders 91 together. A connecting plate 97 welds between the main girders 91 to form a box shaped bridge structure, which is lightweight and has good vertical sectional anti-bending strength and high load-bearing capacity. Four sets of driving mechanism 96 can be synchronously transmitted and installed at the end girders 92, perform motion transmission through friction with the circular guide rail 95, and are configured to enable 0-360 degree rotation of the combinations of rotating beam lines together with the rotating gantries in a horizontal plane, forming two combination of rotating terminal beam lines.

Figure 12:
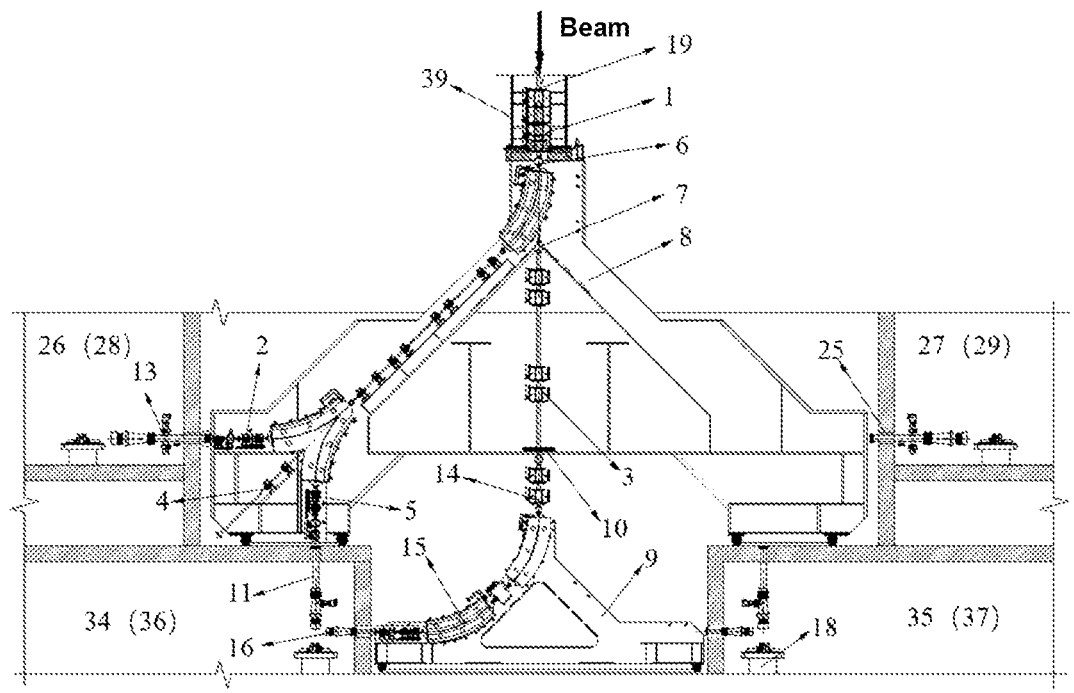
FIG. 12 is a cross section view along a direction of 5-5 or 6-6 in FIG. 11.
Figure 13:
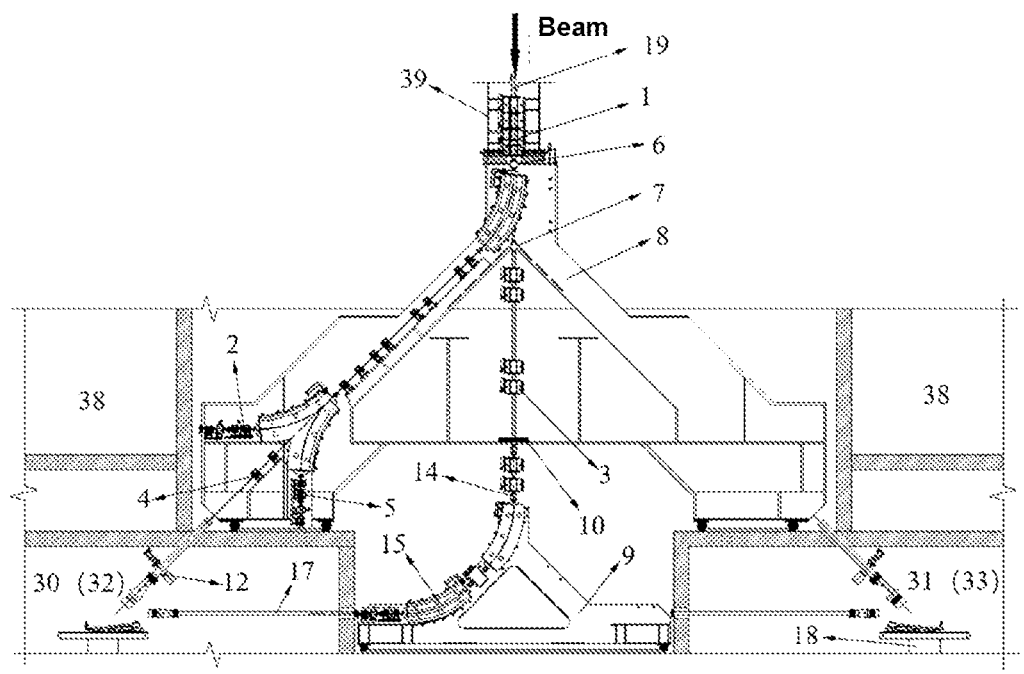
FIG. 13 is a cross section view along a direction of 7-7 or 8-8 in FIG. 11.
Figure 14:
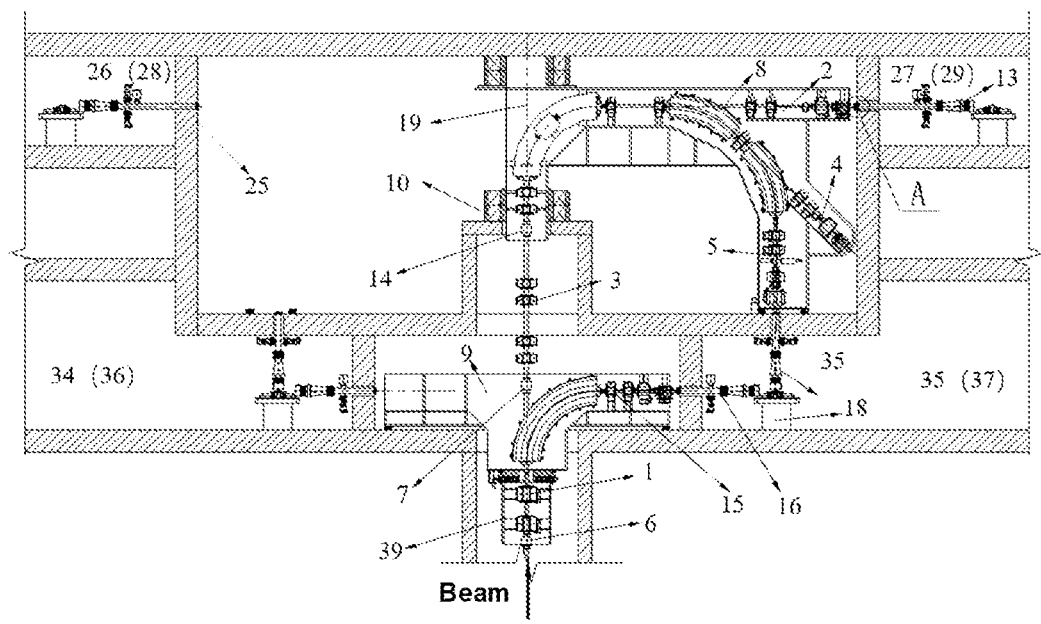
FIGS. 14-15 are cross section views in which a combination of rotating beam lines is fixed on two rotating gantries according to several embodiments of the present disclosure.
Figure 15:
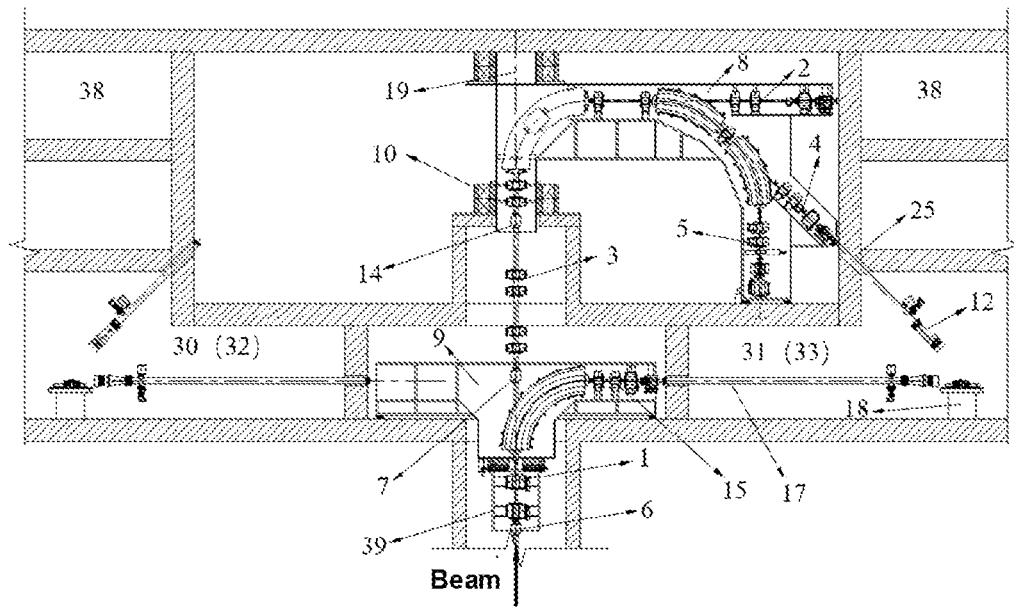

As shown in FIGS. 9-10 and 12-15, the present disclosure provides cross section views in which each of several combinations of rotating beam lines is fixed on two rotating gantries. Specifically, as shown in FIG. 9, the first rotating gantry 8 and the second rotating gantry 9 are arranged in a vertically coaxial manner, and the second rotating gantry 9 is located below the first rotating gantry 8. A combination of rotating beam lines on the first rotating gantry 8 can form horizontal beam lines, vertical beam lines, and 45-degree beam lines or any other angle beam lines in any ways. In order to achieve simultaneous dual-angle irradiation of the patient or a sample in one operation room, a beam led out of the first vertical beam line 3 is deflected to form a second horizontal beam line 15 by means of a deflection dipolar magnet, and the second horizontal beam line 15 is fixed on the second rotating gantry 9. As shown in FIGS. 12 and 13, the second horizontal beam line 15 is connected to the first vertical beam line 3 in a vacuum manner by means of a third dynamic rotation sealing device 14 to ensure that the vacuum is maintained during the relative rotation therebetween. The first vertical beam line 3 is connected to the first rotating gantry 8 through a thrust bearing 10. When rotating at the first rotating gantry 8, the first vertical beam line 3 remains stationary by means of the thrust bearing 10 under the action of gravity.

Figure 10:
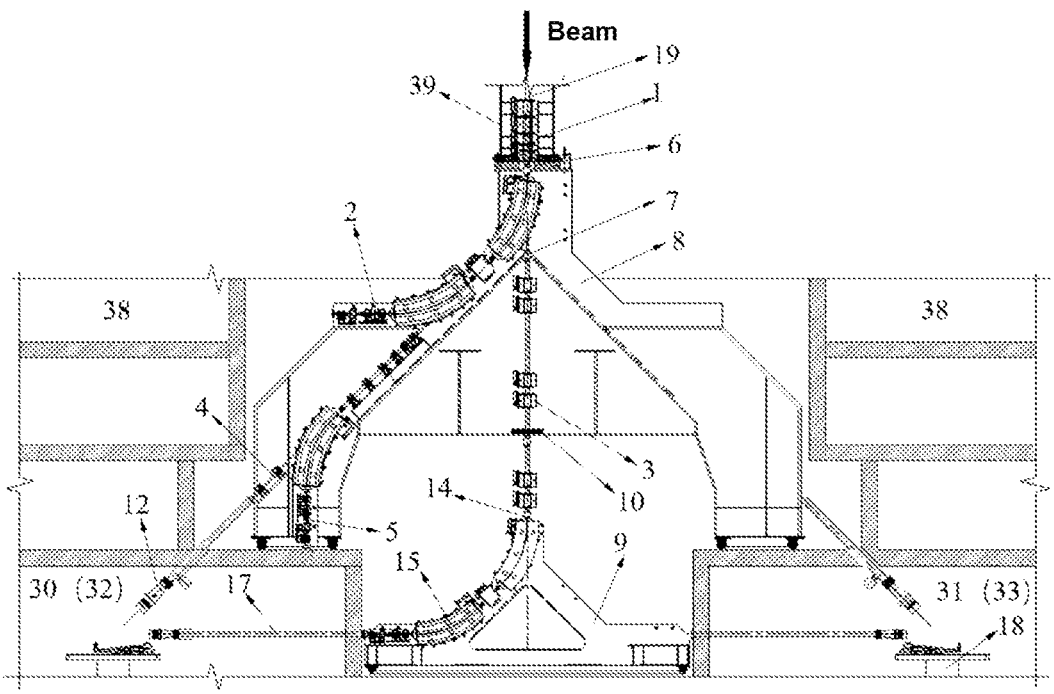
FIG. 10 is a cross section view along a direction of 3-3 or 4-4 in FIG. 8.
Figure 11:
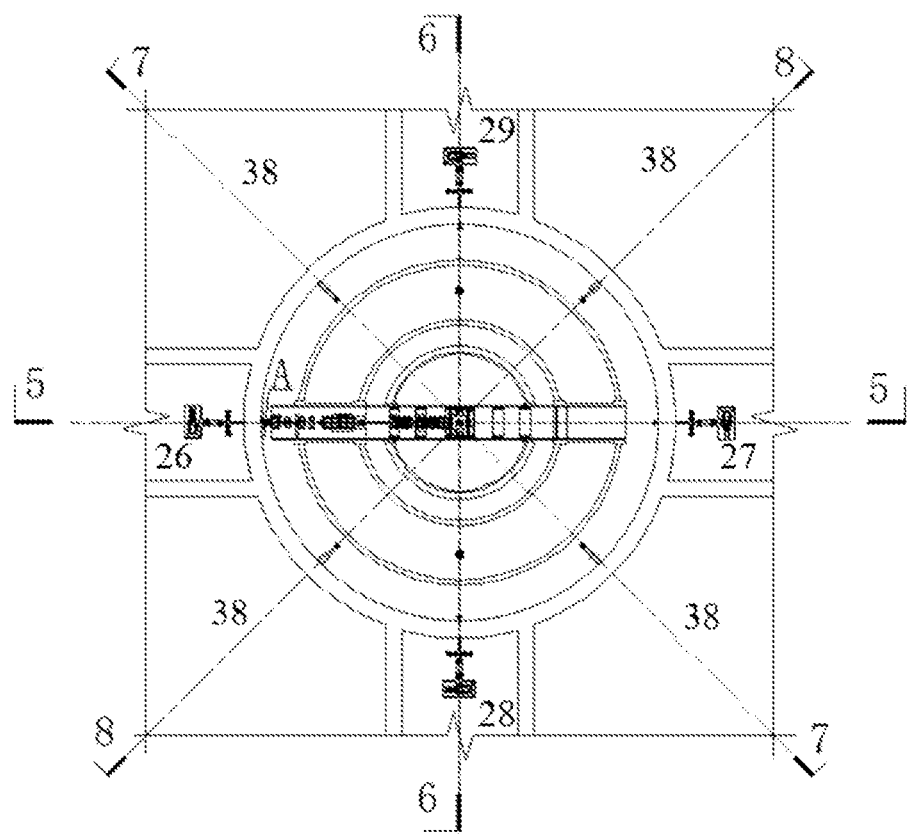
FIG. 11 is a top view in which a combination of rotating beam lines is fixed on two rotating gantries according to a third embodiment of the present disclosure.

As shown in FIGS. 9 and 10, the second horizontal beam line 15 is installed on the second rotating gantry 9, and implements 0-360 degree rotation together with the second rotating gantry 9. The second rotating gantry 9 and the first rotating gantry 8 rotate coaxially, and the two can rotate independently or synchronously. A second horizontal irradiation head 16 is installed in each of the first to fourth vertical-plus-horizontal operation rooms 34-37 in the lower layer through an installation hole 25, thereby forming dual irradiation angles in the same operation room together with a vertical irradiation head 11 (which is a vertical irradiation head corresponding to a vertical beam line that is branched out from a 45-degree beam line fixed on the first rotating gantry 8). A 45-degree operation room 30 and a vertical operation room 34 in the lower layer are arranged in a staggered manner, so that a third horizontal irradiation head 17 can be installed in each of the first to fourth 45-degree-plus-horizontal operation rooms 30-33 in the lower layer. The third horizontal irradiation head 17 and a 45-degree irradiation head 12 form dual irradiation angles in the same operation room.

Figure 16:
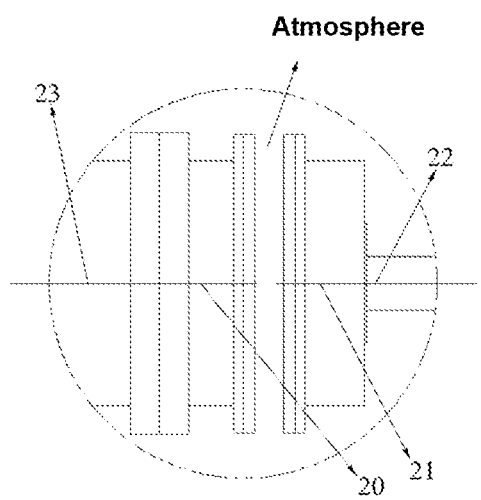
FIG. 16 is a partially enlarged view of A in each of FIGS. 4, 6, 7, 8, 11, and 14.

As shown in FIGS. 9-10 and 12-15, the reference numbers 11-13 and 16-17 indicate those separated irradiation heads at different angles, which are fixedly installed inside the operation rooms through the installation holes 25 in the operation rooms. The rotating gantry is powered by a circular sliding contact line 24, and 0-360 degree rotation of the combination of rotating beam lines is enabled under the action of the driving mechanisms 96. A first vacuum film window 20 and a second vacuum film window 21 are used between the combination of rotating beam lines and the irradiation heads 11-13 and 16-17 mounted at fixed angles to achieve vacuum sealing and physical space separation. As shown in FIG. 16, an ion beam can pass through the first vacuum film window 20, the atmosphere, and the second vacuum film window 21 in turn from the combination of rotating beam lines to the irradiation heads in a non-destructive manner. Compared to a terminal treatment system with fixed beam lines, the terminal treatment system of the present disclosure in which the combination of rotating beam lines are fixed on two rotating gantries can provide more operation rooms, preferably up to 12, a length of the beam lines is only about 10% of the conventional beam lines, the treatment angles cover all treatment angles of the conventional beam line arrangement, and can further provide eight dual-angle operation rooms. Apparently, the irradiation heads and the terminal beam lines in the present disclosure can be connected in a fixed manner, that is, there is no vacuum film window between the irradiation heads 11-13, 16-17 and the terminal beam lines, which can also achieve the arrangement of a plurality of operation rooms in the terminal treatment system.

Specifically, as shown in FIGS. 8-15, provided are several terminal irradiation systems each having a plurality of combinations of rotating beam lines (with beam lines being fixed on two rotating gantries). Apparently, any other beam line combination that can achieve this irradiation effect is also feasible, and will not be described in detailed here. Said terminal irradiation system with the plurality of combinations of rotating beam lines can provide four 45-degree-plus-horizontal irradiation angles, four vertical-plus-horizontal irradiation angles, and four horizontal irradiation angles. A tumor patient can complete the required multiple irradiation angles in one operation room at a time, thereby further improving treatment efficiency. According to an arrangement of the operation rooms and treatment needs, more of the above operation rooms can also be configured.

In addition, on the basis of the combination of rotating beam lines, more single combination of rotating beam lines or more the plurality of combinations of rotating beam lines can be provided to form a rotating beam line group. The plurality of combinations of rotating beam lines can be arranged coaxially, and a plurality of rotating beam lines can rotate independently or synchronously. These rotating beam lines can not only expand the number of the operation rooms as well as irradiation angles therein, but also intersect with one another to form a layout in which there are multiple irradiation angles in one operation room.

Figure 17:
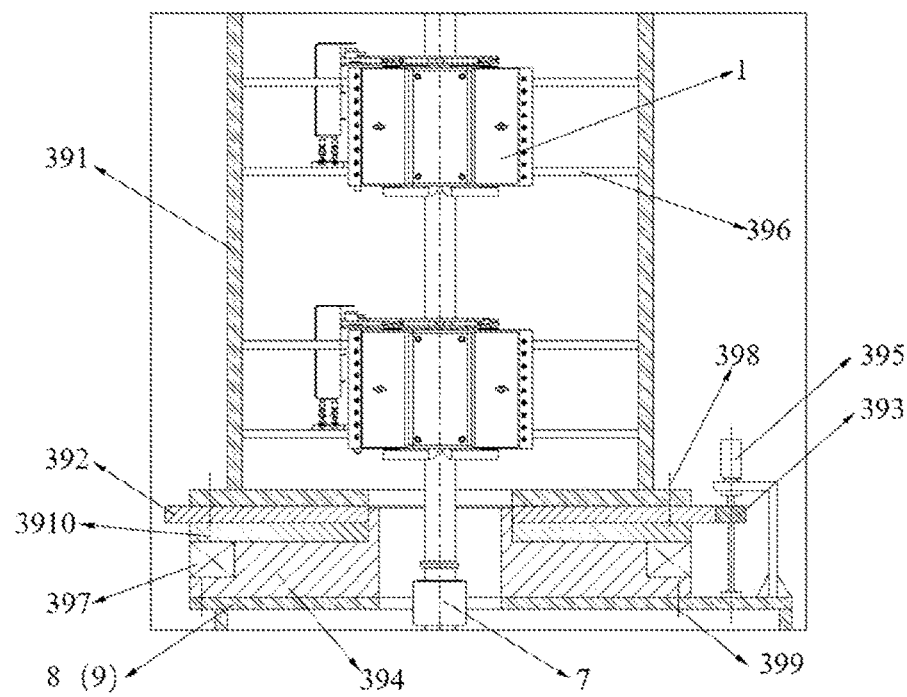
FIG. 17 is a partially enlarged view of B in FIG. 9.

As shown in FIGS. 2 and 17, the rotator beam line 1 of the present disclosure is connected to the first rotating gantry 8 or the second rotating gantry 9 through a rotating mechanism 39. The rotating mechanism 39 includes: a rotating cylinder 391 for installing and fixing several quadrupole magnets on the rotator beam line 1; a large gear 392, which is connected to the rotating cylinder 391 via a first bolt 398; a gear shaft 393, which is meshed with the large gear 392; and a positioning shaft 394, which is securely connected to the first rotating gantry 8 or the second rotating gantry 9 via a second bolt 399, the large gear 392 being connected to the positioning shaft 394 by means of a spacer flange 3910 and a bearing 397. The several quadrupole magnets on the rotator beam line 1 are fixedly installed inside the rotating cylinder 391 via a fixing bracket 396. The rotating cylinder 391, the positioning shaft 394 and the rotating gantry are each provided with through holes for accommodating passage of the rotator beam line 1. The gear shaft 393 driven by a motor 395 drives the large gear 392, and the large gear 392 drives the rotating cylinder 391 to enable rotation of several quadrupole magnets on the rotator beam line 1. The rotating mechanism 39 and the rotator beam line 1 form a rotator, which is used to eliminate an impact of beam line rotation on terminal beam spots. The rotator rotates in the same direction as the terminal beam lines, with a rotation angle of ½ of a rotation angle of the terminal beam lines. The several quadrupole magnets in the rotator adopt a mirror symmetric optical design.

The present disclosure provides a compact optical design for implementing a combination of rotating beam lines, which includes a rotator beam line 1 and a plurality of terminal beam lines. The rotator beam line 1 is a general beam line shared by all terminal beam lines (terminal beam lines including a first horizontal beam line 2, a 45-degree beam line 4, a first vertical beam line 3, a second vertical beam line 5, etc.).

Figure 18:
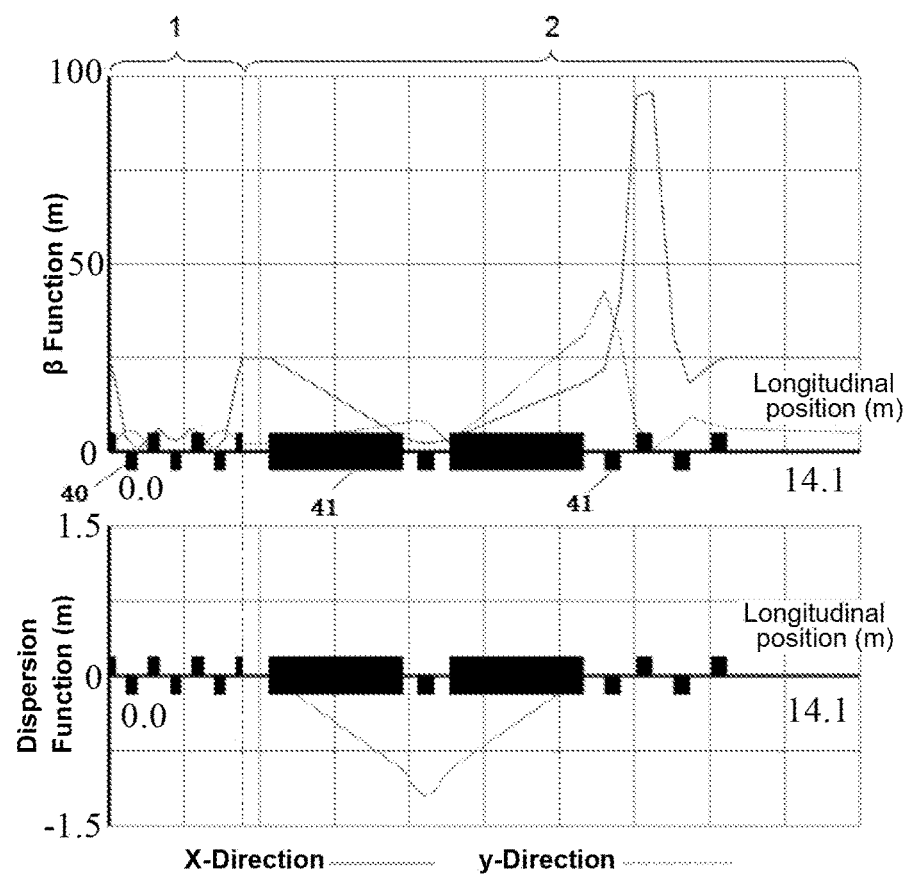
FIG. 18 is an optical parameter diagram of a first horizontal terminal of the present disclosure.

The rotator beam line 1 is a key component for achieving the combination of rotating beam lines, and is used to eliminate the impact of beam line rotation on terminal beam spots. In a specific embodiment of the present disclosure, the rotator beam line 1 is composed of seven quadrupole magnets 40, as shown in FIG. 18. During the rotation, the rotator beam line 1 rotates in the same direction as the terminal beam lines, with a rotation angle of ½ of a rotation angle of the terminal beam lines. The rotator beam line 1 adopts a mirror symmetrical optical design, in which the seven quadrupole magnets 40 are centered around the fourth quadrupole magnet 40, and the remaining six quadrupole magnets 40 are arranged in a mirror symmetrical manner. For a beam at the middle (i.e., the fourth quadrupole magnet), both a Function in x-direction and a Function in y-direction are zero. This beam line has the most striking feature that a phase shift in the x-direction is $2\pi$, a phase shift in the y-direction is 7E, and optical parameters (twist parameters) of an inlet and an outlet are mirror symmetrical. In order to shorten the length of the rotator beam line 1, preferably, the quadrupole magnets 40 all adopt superconducting magnets, with a normalized integral gradient of 2-20/m and a total length of only 2.5 m. Alternatively, a design with room temperature magnets can be used, with a corresponding total length of 10-20 m. The quadrupole magnets 40 can also be applied by a way of a combination of 5-10 pieces. Another prominent advantage of the optical design of said rotator is to adapt to arbitrarily angled terminal beam lines while keeping beam spot sizes of the entire lines small, and the combination of rotating beam lines such as of horizontal, of vertical, and of 45-degree in the present disclosure can simultaneously enable optical parameters to be constant during the rotation of the plurality of arbitrarily angled terminal beam lines.

The terminal beam lines (including the first horizontal beam line 2, the 45-degree beam line 4, the first vertical beam line 3, the second vertical beam line 5, etc.) are configured to allocate a beam transmitted from the rotator beam line 1 to different terminals, and perform matching with a scanning area according to a target size required by a terminal.

Figure 23:
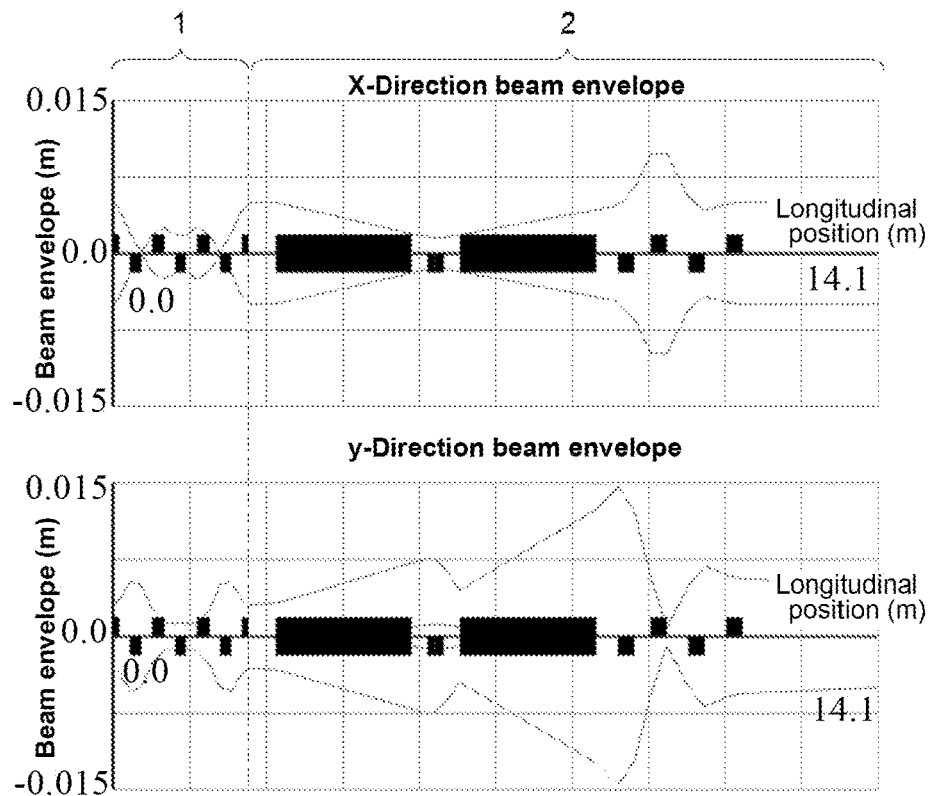
FIG. 23 is a beam envelope diagram of the first horizontal terminal of the present disclosure.

In a specific embodiment of the present disclosure, an optical design of the first horizontal beam line 2 is shown in FIG. 18, and includes two 45-degree dipole magnets 41, as shown by black blocks which are symmetrical relative to the horizontal axis (abscissa) in the figure, and five quadrupole magnets 40, as shown in black blocks distributed on both upper and lower sides of the horizontal axis (abscissa) in the figure, where the black blocks located above the horizontal axis represent focusing quadrupole magnets, and the black blocks located below the horizontal axis represent defocused quadrupole magnets. The two 45-degree dipole magnets 41 are configured to deflect the beam to a horizontal direction, and forms a de-dispersion structure with a quadrupole magnet 40 (the first quadrupole magnet from the left in the horizontal axis) at the same time. The second to fifth quadrupole magnets 40 are configured to perform terminal beam spot matching. A normalized integral gradient of the quadrupole magnets 40 is 0.5-5/m. The first horizontal beam line 2 adopts a compact design, with a total length of less than 15 m. A beam envelope thereof is shown in FIG. 23, and transverse dimension of beam of the entire line is less than ±15 mm.

In FIG. 18, a dash curve in the upper half of the first horizontal beam line 2 represents a y-direction $\beta$ Function, a solid curve represents a x-direction $\beta$ Function, the functions respectively indicate a dimension relationship between the x-direction and the y-direction when the beam is stably transmitted in the first horizontal beam line 2. The dash curve in the lower half represents a y-direction dispersion function, which indicates that fluctuation of y-direction motion trajectory that is superimposed on the beam due to an impact of momentum dispersion on the beam. In the embodiment of the present disclosure, an x-direction dispersion function of the first horizontal beam line 2 is always zero. From the optical diagram, it can be determined that transition of the $\beta$ Function is smooth, which ensures the stability of the optical structure. The optical diagrams in FIGS. 19-22 can also deduce conclusions similar to that of FIG. 18.

Figure 19:
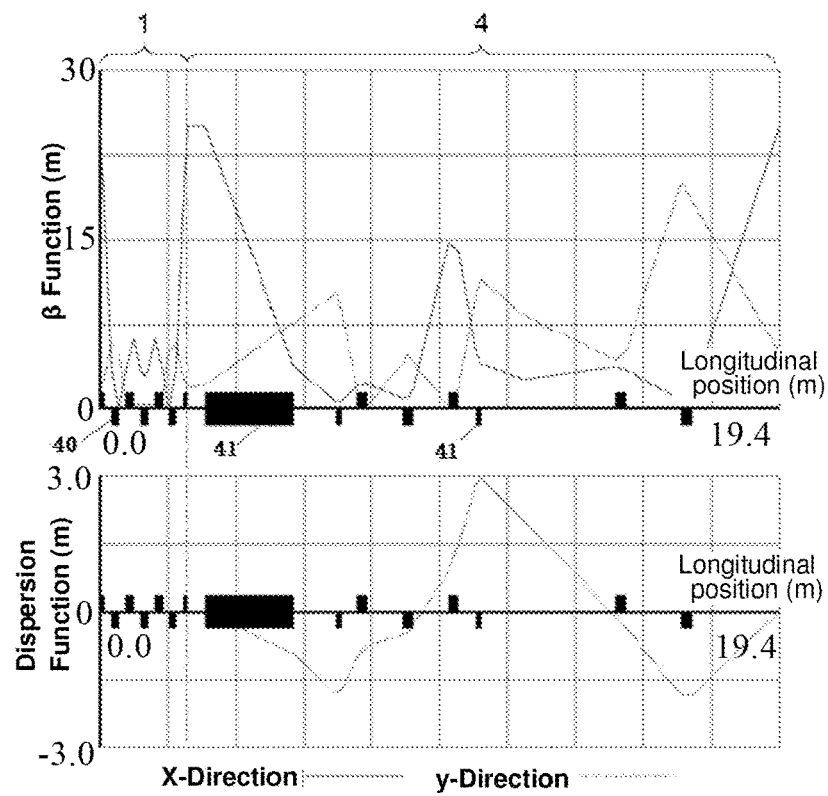
FIG. 19 is an optical parameter diagram of a first 45-degree terminal of the present disclosure.
Figure 24:
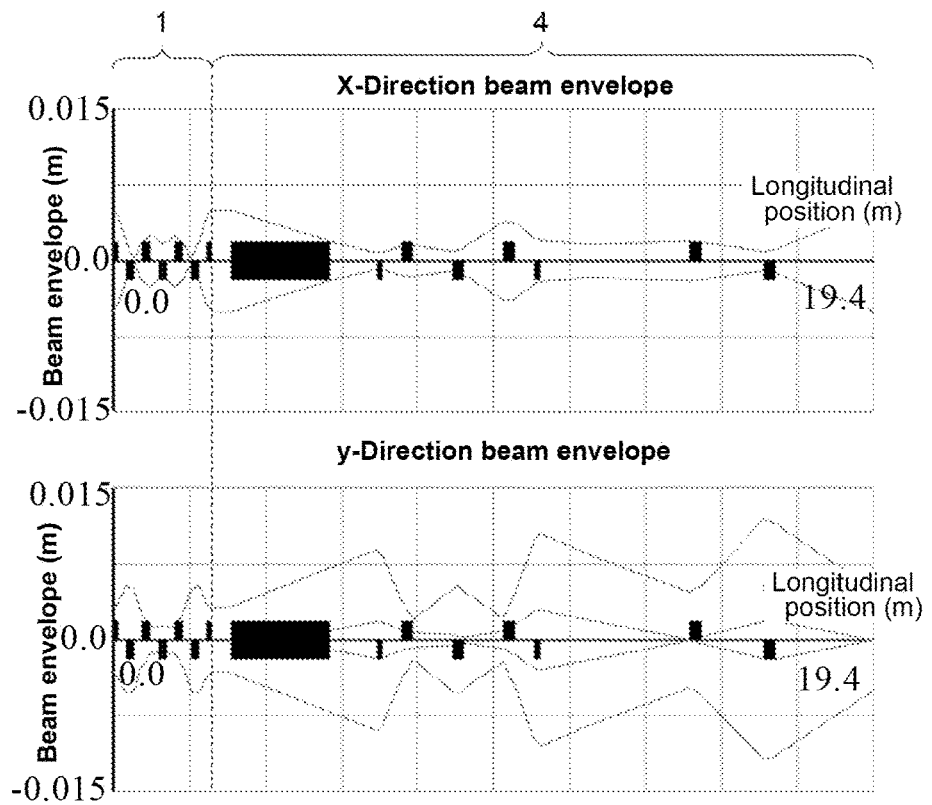
FIG. 24 shows a beam envelope diagram of the first 45-degree terminal of the present disclosure.

In a specific embodiment of the present disclosure, an optical design of the 45-degree beam line 4 is shown in FIG. 19, including one 45-degree dipole magnet 41 and seven quadrupole magnets 40. The one 45-degree dipole magnet 41 is configured to deflect the beam to a 45-degree direction, and the quadrupole magnets 40 are configured to perform terminal beam spot matching and reduce terminal dispersion to zero. A normalized integral gradient of the quadrupole magnets 40 is 0.5-5/m. The terminal beam lines adopt a compact design, with a total length of less than 20 m. A beam envelope thereof is shown in FIG. 24, and transverse dimension (x-direction and y-direction) of beam of the entire line is less than ±15 mm.

Figure 20:
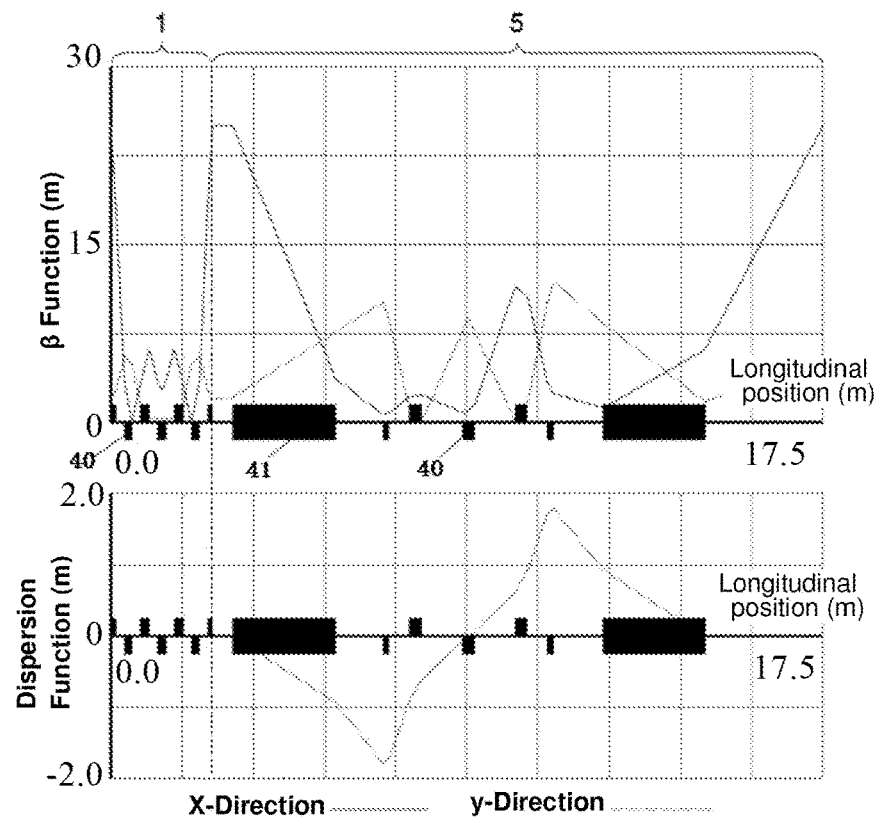
FIG. 20 is an optical parameter diagram of a first vertical terminal of the present disclosure.
Figure 25:
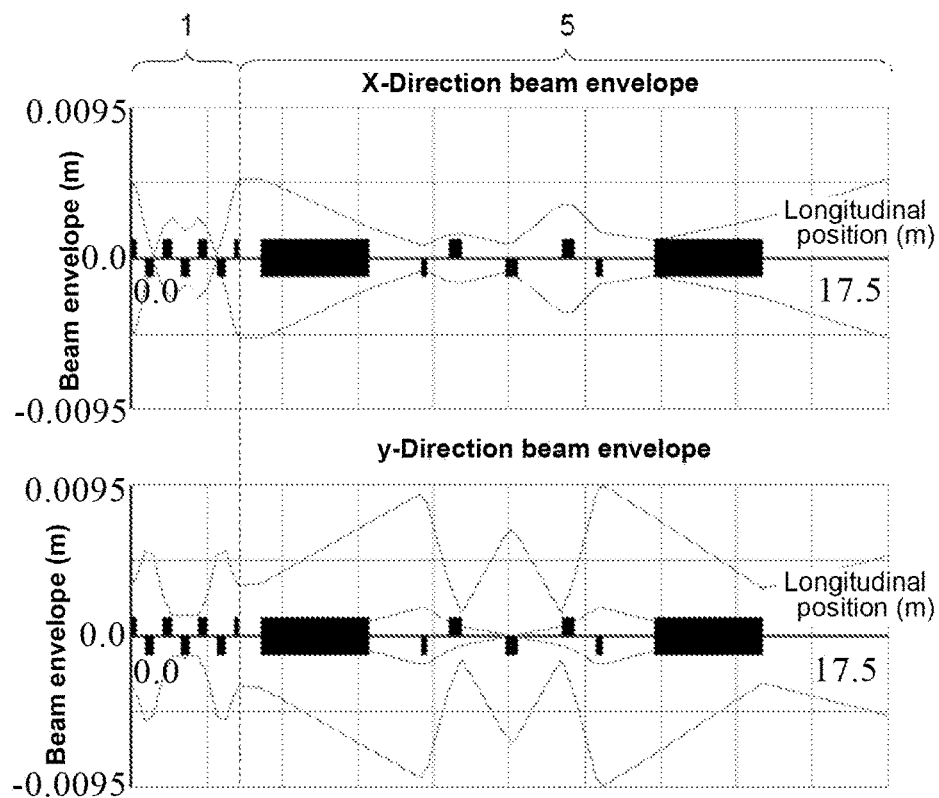
FIG. 25 shows a beam envelope diagram of the first vertical terminal of the present disclosure.

In a specific embodiment of the present disclosure, an optical design of the second vertical beam line 5 is shown in FIG. 20, including two 45-degree dipole magnets 41 and five quadrupole magnets 40. The two 45-degree dipole magnets 41 with opposite deflection directions with each other are configured to deflect the beam to a vertical direction, and the quadrupole magnets 40 and the 45-degree dipole magnets 41 form an de-dispersion structure and are configured to perform terminal beam spot matching. A normalized integral gradient of the quadrupole magnets 40 is 0.5-5/m. The terminal beam lines adopt a compact design, with a total length of less than 18 m. A beam envelope thereof is shown in FIG. 25, and transverse dimension of beam of the entire line is less than ±15 mm.

Figure 21:
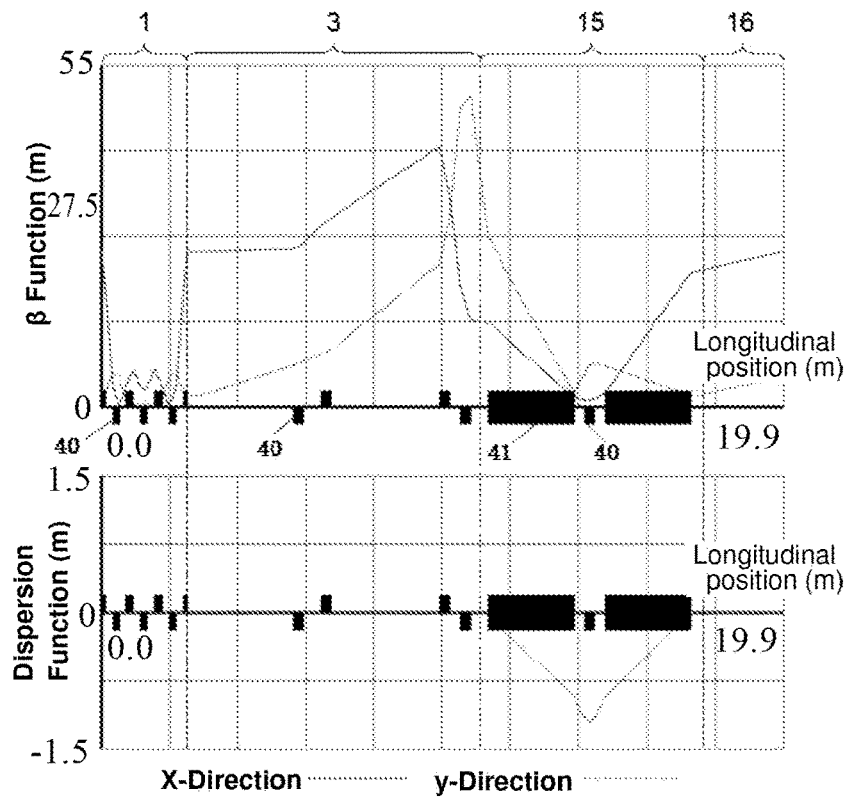
FIG. 21 is an optical parameter diagram of a second horizontal terminal of the present disclosure.
Figure 26:
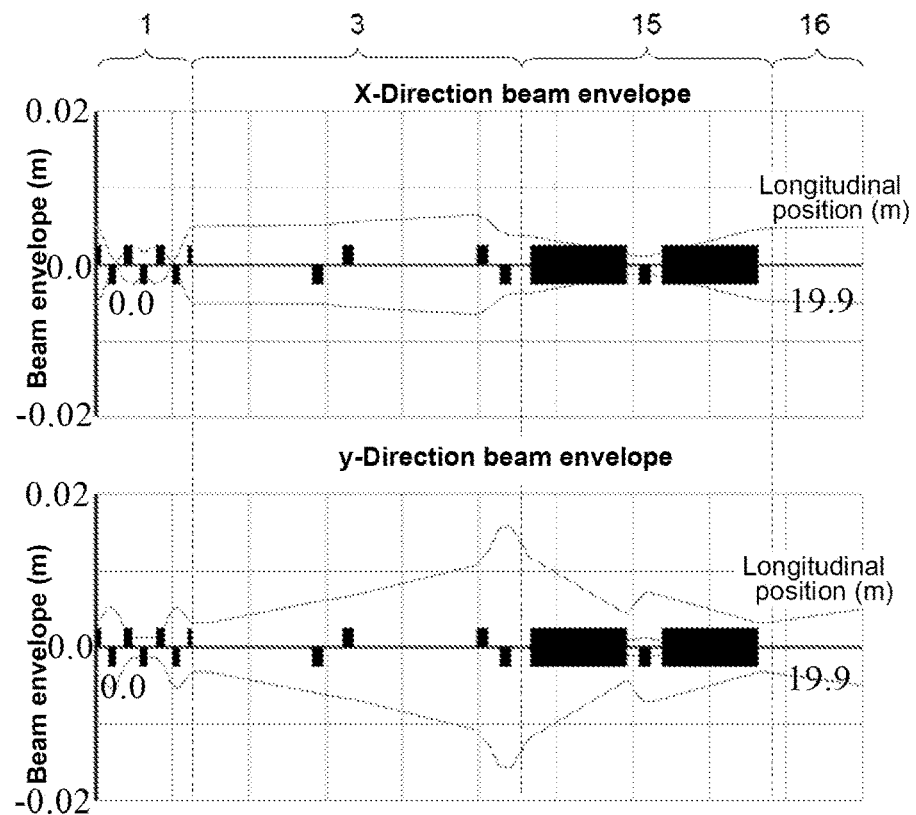
FIG. 26 shows a beam envelope diagram of the second horizontal terminal of the present disclosure.

In a specific embodiment of the present disclosure, an optical design of the second horizontal beam line 15 is shown in FIG. 21, including four quadrupole magnets 40 of the first vertical beam line 3, which are configured to perform beam matching with the second horizontal beam line 15; two 45-degree dipole magnets 41 and one quadrupole magnet 40 of the second horizontal beam line 15, which form an de-dispersion structure; and a second horizontal irradiation head 16 which is a drift joint for beam matching. A normalized integral gradient of the quadrupole magnets 40 is 0.5-5/m. The terminal beam lines adopt a compact design, with a total length of less than 20 m. A beam envelope thereof is shown in FIG. 26, and transverse dimension of beam of the entire line is less than ±16 mm.

Figure 22:
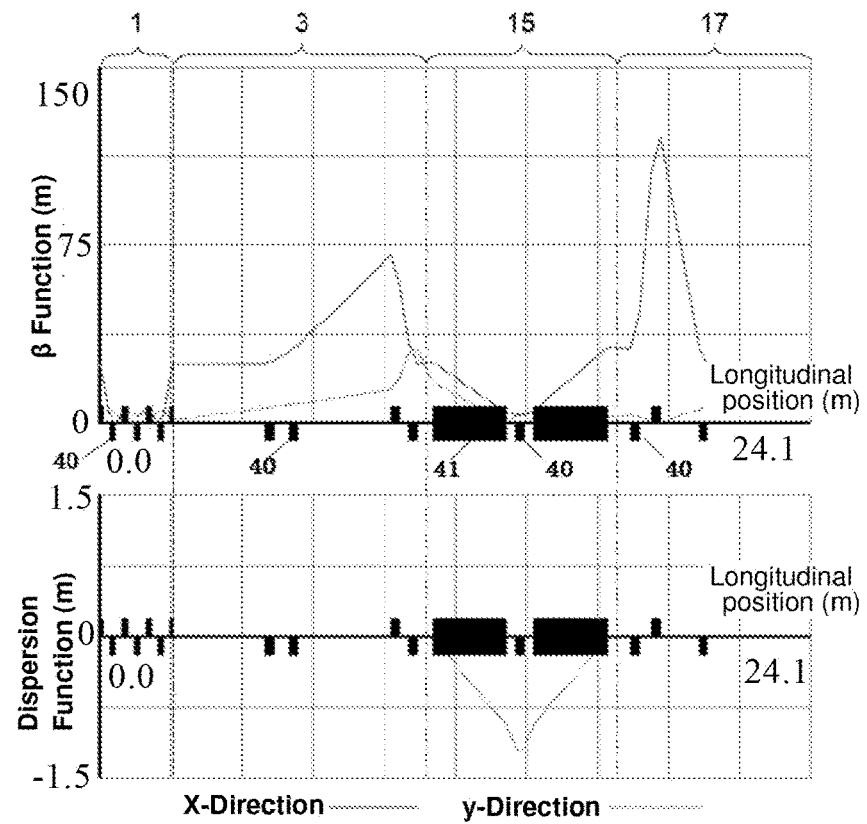
FIG. 22 is an optical parameter diagram of a third horizontal terminal of the present disclosure.
Figure 27:
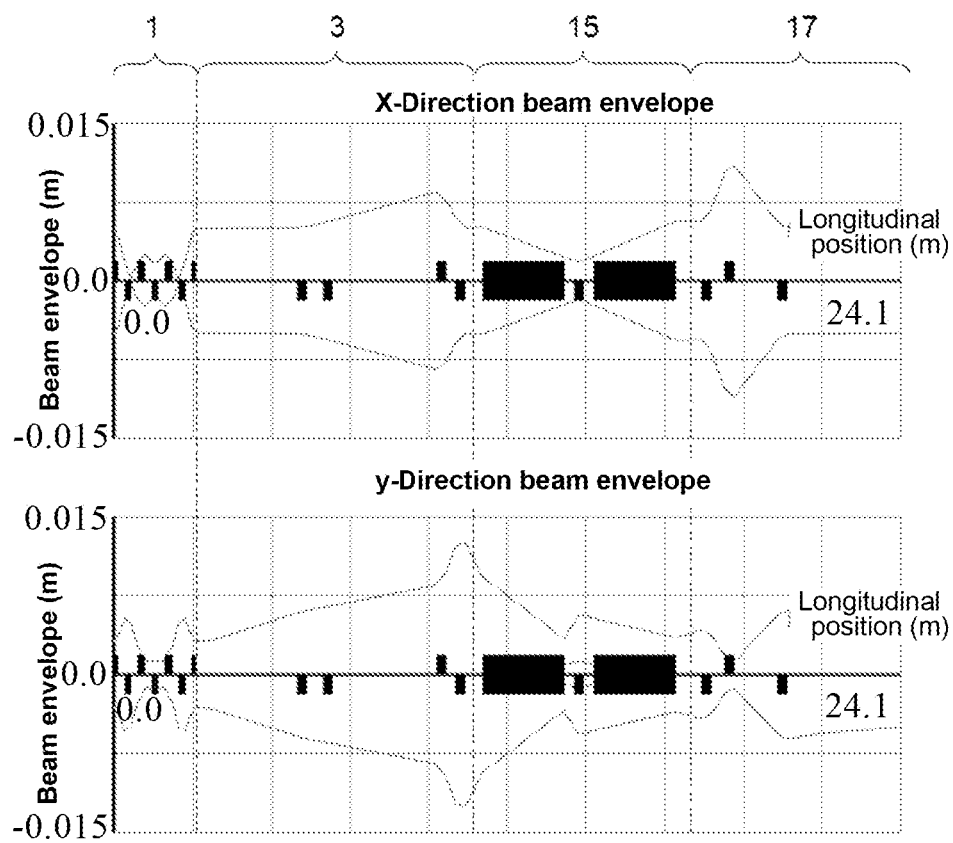
FIG. 27 shows a beam envelope diagram of the third horizontal terminal of the present disclosure.

In a specific embodiment of the present disclosure, an optical design of the third horizontal beam line is shown in FIG. 22, including the beam lines 1, 3, 15 that are shared with the second horizontal beam line 15; and a third horizontal irradiation head 17, the third horizontal irradiation head 17 including three quadrupole magnets 40 for target beam matching. A normalized integral gradient of the quadrupole magnets 40 is 0.5-5/m. The terminal beam lines adopt a compact design, with a total length of less than 25 m. A beam envelope thereof is shown in FIG. 27, and transverse dimension of beam of the entire line is less than ±15 mm.

Furthermore, the transverse dimensions of beams of a horizontal-plus-vertical dual-angle irradiation beam line composed of the first vertical beam line 3 and the second horizontal beam line 15, a horizontal-plus-45-degree dual-angle irradiation beam line composed of the 45-degree beam line 4 and the third horizontal beam line, and all other beam lines each are less than ±16 mm. As such, it is possible to significantly reduce the size and the cost of the magnetic elements, and the prices of related power supply and auxiliary facilities are also significantly reduced accordingly.

The upper half of FIG. 23 represents dimension variation in the x-direction of the beam in the first horizontal beam line 2, while the lower half represents dimension variation in the y-direction of the beam in the first horizontal beam line 2. The dimension of beam determines sizes of the magnetic elements and the vacuum elements, which thereby determines the cost of a hardware system. The first horizontal beam line 2 adopts a compact design, in which the dimensions in both x-direction and y-direction of the beam are less than ±15 mm. Relative to the conventional beam dimension of ±30 mm, the beam dimensions is significantly reduces, thereby significantly reducing the cost of the hardware system. The optical diagrams in FIGS. 24-27 can also deduct conclusions similar to that of FIG. 23.

A second aspect of the present disclosure further provides an operation method for an irradiation terminal, comprising the following steps.

When a tumor patient or a sample requires irradiation, the rotator beam line 1 rotates under the drive of the motor 395 to affect a direction of deflection of a beam, so that the beam is allocated to different beam line terminals. Said combination of rotating beam lines is driven by the driving mechanism 13 to rotate around a rotation axis 19, thereby causing a film window rotating axis 22 to coincide with an vacuum film window axis 23 of an irradiation head;

After the patient or sample is positioned, the desired ion beam passes through the rotator beam line 1, the horizontal beam line 2, and the inclined beam line in sequence, then passes through the first vacuum film window 20 and the second vacuum film window 21, and is finally received by the irradiation head to perform irradiation on the patient or sample.

When irradiation is performed by using the first vertical beam line 3, the ion beam is directly allocated to a related vertical treatment (irradiation) head without passing through the vacuum film windows; when irradiation is performed by selecting the 45-degree (or other angle) beam line 4, the second vertical beam line 5, or the horizontal beam line 2, the desired ion beam passes through the rotator beam line 1, and reaches the terminal beam lines fixed on the rotating system through the first rotary sealing device 6, and upon causing the film window rotating axis 22 to coincide with the vacuum film window axis 23 of an irradiation head through the rotation of the rotating gantry, the ion beam passes through the vacuum film windows therebetween and reaches the treatment (irradiation) head for irradiation.

A third aspect of the present disclosure relates to an application of the irradiation terminal on radiotherapy and industrial irradiation.

The above embodiments are only used to illustrate the situation where any type of accelerator of the present disclosure is vertically downward or horizontally led out and then is deflected to a vertical downward direction. Apparently, all constructions of the present disclosure are also applicable to the situation where any type of accelerator is vertically upwards or horizontally led out and then is deflected to a vertical upwards direction, both of which are included within the scope of the present disclosure.

Finally, it should be noted that the above embodiments are only used to illustrate the technical solution of the present disclosure, not to construct limitation thereto. Although the present disclosure has been described in detail with reference to the aforementioned embodiments, the ordinary technical personnel in the pertinent field should understand that it is still possible to perform modification on the technical solutions described in the aforementioned embodiments or perform equivalent replacement of some technical features, and these modification or replacement shall not exclude the essence of the related technical solutions out of the spirit and scope of the various embodiments of the present disclosure.

What is claimed is:

1. An irradiation terminal based on a combination of rotating beam lines, comprising:
   a combination of rotating beam lines, which is fixed on a first rotating gantry, and includes a rotator beam line and terminal beam lines, wherein the terminal beam lines include a horizontal beam line and an inclined beam line at a certain angle to the ground, the horizontal beam line and the inclined beam line are branches of the rotator beam line;
   the first rotating gantry, including two end girders and two parallel arranged main girders, wherein the two end girders are arranged in gaps at both ends of the two main girders and connected the two main girders together;
   a number of first operation rooms, which are uniformly arranged along a circumferential direction of rotation of the horizontal beam line and form a first layer of operation rooms, a wall of each of the first operation rooms being provided with an installation hole;
   a number of second operation rooms, which are uniformly arranged along a circumferential direction of rotation of the inclined beam line and form a second layer of operation rooms, a wall of each of the second operation rooms being provided with an installation hole;
   a number of irradiation heads, which respectively correspond to the first operation rooms and the second operation rooms in a one-to-one manner, wherein the irradiation heads pass through installation holes to receive ion beams transmitted by the combination of rotating beam lines and then perform irradiation on a patient or sample; and
   a driving mechanism, which is connected to the first rotating gantry in a motion transmission manner and is configured to drive the first rotating gantry to rotate 0-360 degrees along a circular guide rail, so that the combination of rotating beam lines form as beam lines that can rotate 0-360 degrees.

2. The irradiation terminal according to claim 1, wherein the terminal beam lines further includes a first vertical beam line and a second vertical beam line, both of which are branches of the rotator beam line.

3. The irradiation terminal according to claim 2, wherein a flange of an ion beam output of each of the horizontal beam line, the inclined beam line, and the second vertical beam line is equipped with a first vacuum film window, a flange of a receiving end of each of the irradiation heads is equipped with a second vacuum film window, the first vacuum film window and the second vacuum film window are configured to enable vacuum sealing between the combination of rotating beam lines and the irradiation heads.

4. The irradiation terminal according to claim 3, wherein a size of a gap between the first vacuum film window and the second vacuum film window is 5-200 mm.

5. The irradiation terminal according to claim 2, wherein the first vertical beam line is mechanically connected to the first rotating gantry by means of a thrust bearing.

6. The irradiation terminal according to claim 2, wherein the number of rotating gantry is at least one, and when the number of rotating gantry is two, which are the first rotating gantry and the second rotating gantry, respectively, the two are arranged coaxially, the first vertical beam line forms a second horizontal beam line by means of a deflection dipole magnet, the second horizontal beam line is fixed on the second rotating gantry, and an irradiation head of the second horizontal beam line and an irradiation head of the second vertical beam line are located in a same operation room and form vertical and horizontal dual-angle irradiation.

7. The irradiation terminal according to claim 2, wherein the number of rotating gantry is at least one, and when the number of rotating gantry is two, which are the first rotating gantry and the second rotating gantry, respectively, the two are arranged coaxially, the first vertical beam line forms a second horizontal beam line by means of a deflection dipole magnet, the second horizontal beam line is fixed on the second rotating gantry, and an irradiation head of the inclined beam line and a third irradiation head of the second horizontal beam line are located in a same operation room and form inclined and horizontal dual-angle irradiation.

8. The irradiation terminal according to claim 1, wherein each of the main girders includes a vertical girder, a horizontal girder, and two inclined girders connecting the vertical and horizontal girders, the horizontal girders of the two main girders are connected together through a connecting shaft and a connecting plate, and the combination of rotating beam lines is assembled in a cavity formed by the two main girders.

9. The irradiation terminal according to claim 1, wherein the irradiation terminal further comprise moving parts, the moving parts include a slider and a connector which are interconnected with each other, the slider is slidably connected to the circular guide rail, and the connector is connected to the driving mechanism in a motion transmission manner.

10. The irradiation terminal according to claim 1, wherein the rotator beam line enables rotation by means of a rotating mechanism, the rotating mechanism includes a rotating cylinder, a large gear, a gear shaft, and a positioning shaft, wherein the gear shaft and the positioning shaft are securely connected to the rotating gantry, respectively, the large gear is connected to the positioning shaft through a spacer flange and a bearing, the large gear is meshed with the gear shaft, the large gear is securely connected to the rotating cylinder, the rotating cylinder is configured to fix the rotator beam line, and the rotating cylinder, the positioning shaft, and the rotating gantry each are provided with through holes for accommodating passage of the rotator beam line.

11. The irradiation terminal according to claim 1, wherein the rotator beam line has a direction of rotation identical with the terminal beam lines, with a rotation angle of ½ of a rotation angle of the terminal beam lines, and the rotator beam line has an x-direction phase shift that is of even multiple of $\pi$ and a $\gamma$-direction phase shift that is of an odd multiple of $\pi$, so as to achieve optical invariance during rotation of the terminal beam lines.

12. The irradiation terminal according to claim 1, wherein the irradiation heads and the combination of rotating beam lines are designed in an integrated manner or a separated manner.

\* \* \* \* \*